(12) United States Patent
Nagai et al.

(10) Patent No.: US 7,144,579 B2
(45) Date of Patent: Dec. 5, 2006

(54) PARAMYXOVIRUSES COMPRISING MODIFIED TRANSCRIPTION START SEQUENCE

(75) Inventors: Yoshiyuki Nagai, Toyama (JP); Atsushi Kato, Tokyo (JP); Mamoru Hasegawa, Ibaraki (JP); Makoto Inoue, Ibaraki (JP)

(73) Assignee: DNAVEC Research, Inc., Ibaraki (JP)

( * ) Notice: Subject to any disclaimer, the term of this patent is extended or adjusted under 35 U.S.C. 154(b) by 731 days.

(21) Appl. No.: 09/979,908

(22) Filed: Nov. 28, 2001

(65) Prior Publication Data

US 2004/0121308 A1    Jun. 24, 2004

Related U.S. Application Data

(63) Continuation-in-part of application No. PCT/JP00/06051, filed on Sep. 6, 2000.

(30) Foreign Application Priority Data

Sep. 6, 1999    (JP)    ................................ 11-252231

(51) Int. Cl.
   C07H 19/00    (2006.01)
   C12N 15/63    (2006.01)
   C12N 15/66    (2006.01)
   A61K 39/12    (2006.01)
   A61K 39/155   (2006.01)

(52) U.S. Cl. ................ 424/211.1; 536/23.1; 435/320.1; 435/91.41; 930/10; 424/199.1

(58) Field of Classification Search .................... None
See application file for complete search history.

(56) References Cited

U.S. PATENT DOCUMENTS 5,993,824 A * 11/1999 Murphy et al. .......... 424/211.1

6,645,760 B1    11/2003 Nagai et al. ................. 435/325
6,723,532 B1    4/2004 Nagai et al. ............... 435/69.1

(Continued)

FOREIGN PATENT DOCUMENTS

EP    0 864 645 A1    9/1998

(Continued)

OTHER PUBLICATIONS

Kato et al. Journal of Virology. Nov. 1999; 73 (11): 9237-9246.*

(Continued)

*Primary Examiner*—Bruce R. Campell
*Assistant Examiner*—Benjamin P. Blumel
(74) *Attorney, Agent, or Firm*—Clark & Elbing LLP

(57) ABSTRACT

The present invention provides virus vectors of the family Paramyxoviridae in which the transcription start (S) sequence has been modified so as to modify the expression of genes located downstream thereof, a method for producing the vectors, and uses thereof. By measuring the transcription initiation efficiency of the S sequence of each gene carried by Sendai viruses (SeV), it was clarified that the S sequence of F gene has a significantly lower ability to promote transcription than the other three S sequences. When the S sequence of the F gene of wild type Sendai virus was substituted by the S sequence of the P/M/HN gene-type showing a high transcription initiation efficiency, the F gene of the resultant Sendai virus mutant and genes located downstream thereof show elevated expression levels. It was also revealed that this mutant proliferates more quickly than the wild type. The vectors of this invention are useful in elevating the expression of foreign genes and producing pharmaceutical compositions and vaccines. Furthermore, by lowering virus gene expression from virus vectors, it is possible to suppress transcription and/or replication and reduce cytotoxicity of the vector genome.

12 Claims, 16 Drawing Sheets

U.S. PATENT DOCUMENTS

| | | | |
|---|---|---|---|
| 6,746,860 B1 | 6/2004 | Tokusumi et al. | 435/320.1 |
| 6,828,138 B1 | 12/2004 | Nagai et al. | 435/235.1 |
| 2002/0002143 A1 | 1/2002 | Kano et al. | 514/44 |
| 2002/0098576 A1 | 7/2002 | Nagai et al. | 435/320.1 |
| 2003/0166252 A1 | 9/2003 | Kitazato et al. | 435/235.1 |
| 2003/0170210 A1 | 9/2003 | Masaki et al. | 424/93.2 |
| 2003/0170266 A1 | 9/2003 | Kitazato et al. | 424/199.1 |
| 2003/0170897 A1 | 9/2003 | Imai et al. | 435/456 |
| 2003/0203489 A1 | 10/2003 | Yonemitsu et al. | 435/456 |
| 2004/0005296 A1 | 1/2004 | Yonemitsu et al. | 424/93.2 |
| 2004/0053877 A1 | 3/2004 | Fukumura et al. | |
| 2004/0101965 A1 | 5/2004 | Griesenbach et al. | |

FOREIGN PATENT DOCUMENTS

| | | |
|---|---|---|
| EP | 0863202 A1 | 9/1998 |
| WO | WO 97/16538 | 9/1997 |

OTHER PUBLICATIONS

Kuo et al. Journal of Virology. 1997; 71 (7): 4944-4953.*

Hoffman and Banerjee, "Precise Mapping of the Replication and Transcription Promoters of Human Parainfluenza Virus Type 3," *Virology* 269:201-211 (2000).

Kato et al., "Sendai Virus Gene Start Signals Are Not Equivalent in Reinitiation Capacity: Moderation at the Fusion Protein Gene," *J. Virol.*, 73:9237-9246 (1999).

Stokes et al., "The Complete Nucleotide Sequence of Two Cold-Adapted, Temperature-Sensitive Attenuated Mutant Vaccine Viruses (cp12 and cp45) Derived from the JS Strain of Human Parainfluenza Virus Type 3 (PIV3)," *Virus Research* 30:43-52 (1993).

Nagai et al., U.S. Appl. No. 09/132,521, filed Aug. 11, 1998.
Nagai et al., U.S. Appl. No. 09/471,840, filed Dec. 23, 1999.
Tokusumi et al., U.S. Appl. No. 09/702,498, filed Oct. 31, 2000.
Nagai et al., U.S. Appl. No. 09/728,207, filed Dec. 1, 2000.
Kano, et al., U.S. Appl. No. 09/823,699, filed Mar. 30, 2001.
Yonemitsu et al., U.S. Appl. No. 10/111,356, filed Jul. 30, 2002.
Masaki et al., U.S. Appl. No. 10/181,646, filed Nov. 22, 2002.
Yonemitsu et al., U.S. Appl. No. 10/306,949, filed Nov. 29, 2002.
Imai et al., U.S. Appl. No. 10/312,476, filed Apr. 10, 2003.
Kitazato et al., U.S. Appl. No. 10/316,535, filed Dec. 10, 2002.
Kitazato et al., U.S. Appl. No. 10/316,538, filed Dec. 10, 2002.
Fukumura et al., U.S. Appl. No. 10/398,598, filed Apr. 3, 2003.
Griesenbach et al., U.S. Appl. No. 10/416,252, filed May 8, 2003.
Yonemitsu et al., U.S. Appl. No. 10/444,661, filed May 23, 2003.
Conzelmann, "Nonsegmented Negative-Strand RNA Viruses: Genetics and Manipulation of Viral Genomes," *Ann. Rev. Genet.*, 32: 123-162 (1998).

Hasan et al., "Creation of an Inectious Recombinant Sendai Virus Expressing the Firefly Luciferase Gene from the 3' Proximal First Locus," *J. of General Virology*, 78: 2813-2820 (1997).

Kuo et al., "Effect of Mutations in the Gene-Start and Gene-End Sequence Motifs on Transcription of Monocistronic and Dicistronic Minigenomes of Respiratory Syncytial Virus," *J. of Virology*, 70(10): 6892-6901 (1996).

Kuo et al., "Analysis of the Gene Start and Gene End Signals of Human Respiratory Syncytial Virus: Quasi-Templated Initiation at Position 1 of the Encoded mRNA," *J. of Virology*, 71(7): 4944-4953 (1997).

Rassa and Parks, "Molecular Basis for Naturally Occurring Elevated Readthrough Transcription Across the M-F Junction of the Paramyxovirus SV5," *Virology* 247: 274-286 (1998).

Stillman and Whitt, "Mutational Analyses of the Intergenic Dinucleotide and the Transcriptional Start Sequence of Vesicular Stomatitis Virus (VSV) Define Sequences Required for Efficient Termination and Initiation of VSV Transcripts," *J. of Virology*, 71(3): 2127-2137 (1997).

Nagai et al., U.S. Appl. No. 09/471,840, filed Dec. 23, 1999.
Nagai et al., U.S. Appl. No. 09/728,207, filed Dec. 1, 2000.
Kano, et al., U.S. Appl. No. 09/823,699, filed Mar. 30, 2001.
Masaki et al., U.S. Appl. No. 10/181,646, filed Nov. 22, 2002.
Yonemitsu et al., U.S. Appl. No. 10/306,949; filed Nov. 29, 2002.
Imai et al., U.S. Appl. No. 10/312,476, filed Apr. 10, 2003.
Kitazato et al., U.S. Appl. No. 10/316,535, filed Dec. 10, 2002.
Kitazato et al., U.S. Appl. No. 10/316,538, field Dec. 10, 2002.
Yonemitsu et al., U.S. Appl. No. 10/444,661, filed May 23, 2003.
Conzelmann, "Nonsegmented Negative-Strand RNA Viruses: Genetics and Manipulation of Viral Genomes," *Ann. Rev. Genet.*, 32: 123-162 (1998).

Hasan et al., "Creation of an Inectious Recombinant Sendai Virus Expressing the Firefly Luciferase Gene from the 3' Proximal First Locus," *J. of General Virology*, 78: 2813-2820 (1997).

Kuo et al., "Effect of Mutations in the Gene-Start and Gene-End Sequence Motifs on Transcription of Monocistronic and Dicistronic Minigenomes of Respiratory Syncytial Virus," *J. of Virology*, 70(10): 6892-6901 (1996).

Kuo et al., "Analysis of the Gene Start and Gene End Signals of Human Respiratory Syncytial Virus: Quasi-Templated Initiation at Position 1 of the Encoded mRNA," *J. of Virology*, 71(7): 4944-4953 (1997).

Rassa and Parks, "Molecular Basis for Naturally Occurring Elevated Readthrough Transcription Across the M-F Junction of the Paramyxovirus SV5," *Virology* 247: 274-286 (1998).

Stillman and Whitt, "Mutational Analyses of the Intergenic Dinucleotide and the Transcriptional Start Sequence of Vesicular Stomatitis Virus (VSV) Define Sequences Required for Efficient Termination and Initiation of VSV Transcripts," *J. of Virology*, 71(3): 2127-2137 (1997).

* cited by examiner

Figure 2 leader  N   P/V/C   M   F   HN   L   trailer 15,384 nt

ACCAAACAGG AGAAAAACA TGTATGGAT ATGTAATGAA GTTATACAGG ATTTT (SEQ ID NO:37)

| | | | | |
|---|---|---|---|---|
| (SEQ ID NO:38) | AGGGTCAAAG | TATC | N | --- | TAG | TAAGAAAAA | CTT | (SEQ ID NO:39) |
| (SEQ ID NO:40) | AGGGTGAAAG | TTCA | P | --- | GAT | TAAGAAAAA | CTT | (SEQ ID NO:41) |
| (SEQ ID NO:42) | AGGGTGAAAG | AAAT | M | --- | AAA | TAAGAAAAA | CTT | (SEQ ID NO:43) |
| (SEQ ID NO:44) | AGGGATAAAG | TCCC | F | --- | TAA | TAAGAAAAA | CTT | (SEQ ID NO:45) |
| (SEQ ID NO:46) | AGGGTGAAAG | TGAG | HN | --- | TAT | TAAGAAAAA | CCC | (SE

PARAMYXOVIRUSES COMPRISING MODIFIED TRANSCRIPTION START SEQUENCE

The application is a continuation-in-part of international patent application serial number PCT/JP00/06051, filed on Sep. 6, 2000, which claims priority from Japanese patent application number 11-252231, filed on Sep. 6, 1999, the disclosures of which are hereby incorporated by reference.

TECHNICAL FIELD

The present invention relates to recombinant viruses of Paramyxoviridae comprising a modified transcription start sequence.

BACKGROUND ART

Paramyxoviruses have a non-segmented negative strand RNA as the genome. Six genes are coded in the genome, and a short sequence (E-IG-S signal) is commonly linked to each gene. These signal sequences are highly conserved especially within a genus and within a family, and is extremely high among genes of a given virus species (Feldmann, H. E. et al., 1992, Virus Res. 24:1–19).

Sendai virus (SeV), classified into Respirovirus in the family Paramyxoviridae, is an enveloped, non-segmented negative-strand RNA virus that is considered to be the prototype for the subfamily Paramyxovirinae. The SeV genome is 15,384 bases in size, starting with a short 3' leader region, followed by six genes encoding the N (nucleocapsid), P (phospho), M (matrix), F (fusion), HN (hemagglutinin-neuraminidase) and L (large) proteins, and ending with a short 5' trailer region. In addition to the P protein, the second gene expresses the accessory V and C proteins by a process known as co-transcriptional editing that inserts a G residue not comprised in the template (Park, K. H. and M. Krystal, 1992, J. Virol. 66:7033–7039; Paterson, R. G., and R. A. Lamb, 1990, J. Virol. 64:4137–4145; Thomas, S. M. et al., 1988, Cell, 54:891–902; Vidal, S. et al., 1990, J. Virol. 64:239–246) and by alternative translational initiations, respectively (Gupta, K. C., and E. Ono, 1997, Biochem. J. 321:811–818; Kuronati, A. et al., 1998, Genes Cells 3:111–124). The genome is tightly associated with the N protein, forming a helical ribonucleoprotein (RNP) complex. This RNP, but not the naked RNA, is the template for both transcription and replication (Lamb, R. A., and D. Kolakofsky, 1996, *Paramyxoviridae:* The viruses and their replication. pp. 1177–1204. In Fields Virology, 3rd edn. Fields, B. N., D. M. Knipe, and P. M. Howley et al. (ed.), Raven Press, New York, N.Y.) There is only a single promoter at the 3' end for viral RNA polymerase comprising the P and L proteins (Hamaguchi, M. et al., 1983, Virology 128:105–117). By recognizing the short, conserved transcription end (E) sequence and transcription start (S) sequence at each gene boundary, the polymerase produces leader RNA and each of the mRNAs (Glazier, K. et al., 1997, J. Virol. 21:863–871). There is a trinucleotide intergenic (IG) sequence between the E sequence and S sequence, which is not transcribed (Gupta, K. C., and D. W. Kingsbury, 1984, Nucleic Acids Res. 12:3829–3841; Luk, D. et al., 1987, Virology 160:88–94). Since the efficiency of reinitiating transcription at each gene boundary is high but not perfect, the transcripts from the downstream genes are less abundant than those from the upstream genes. Therefore, each mRNA is not synthesized in equimolar quantities in infected cells, but there is a polar attenuation of transcription toward the 5' end (Glazier, K. et al., 1997, J. Virol. 21:863–871; Homann, H. E. et al., 1990, Virology 177: 131–140; Lamb, R. A., and D. Kolakofsky, 1996, *Paramyxoviridae:* The viruses and their replication. pp. 1177–1204. In Fields Virology, 3rd edn. Fields, B. N., D. M. Knipe, and P. M. Howley et al. (ed.), Raven Press, New York, N.Y.).

After the translation of the mRNAs and accumulation of translation products, genome replication takes place. Here, the same viral RNA polymerase conducts replication using the same RNP template, but now somehow ignores the respective E sequence and S sequence of each mRNA and generates a full length antigenomic positive sense (+)RNP (Lamb, R. A., and D. Kolakofsky, 1996, *Paramyxoviridae:* The viruses and their replication. pp. 1177–1204. In Fields Virology, 3rd edn. Fields, B. N., D. M. Knipe, and P. M. Howley et al. (ed.), Raven Press, New York, N.Y.). The polymerase enters the promoter at the 3' end of (+)RNP to generate genomic (-) RNP, which serves as the template for the next round of transcription and replication.

The B sequence (3'-AUUCUUUUUU-5' (SEQ ID NO: 26) in the genomic negative sense) is completely conserved among the six genes in the SeV genome. The five U residues in the latter half are thought to allow the polymerase slippage-generating poly(A). In contrast, the S sequences are slightly varied and are generalized as 3'-UCCCWVUUWC-5' (SEQ ID NO: 27) (Gupta, K. C., and D. W. Kingsbury, 1984, Nucleic Acids Res. 12:3829–3841). Specifically, the S sequence is UCCCACUIJUC (SEQ ID NO: 28) for P, M and HN genes, UCCCAgUUUC (SEQ ID NO: 29) for N gene, UCCCuaUUUC (SEQ ID NO: 30) for F gene, and UCCCACUUaC (SEQ ID NO: 31) for L gene. Identical differences are seen in all SeV strains sequenced to date, regardless of differences in isolation procedure, passage history, and virulence for the natural host such as mice, suggesting that the variations are locus-specific. It is possible that these differences arise as a result of nucleotide accumulation in sites that are unaffected by variations in the S sequence. Another possibility is that these differences arise due to nucleotide substitutions at important sites of the signal and the selection of viruses that have acquired the ability to regulate the expression of each gene during viral evolution.

Up to now, several studies with model template systems of various nonsegmented negative strand RNA viruses have indicated that the S sequences are indeed critical for transcriptional initiation, but sequence variations are tolerated to some extent (Barr, J. N. et al., 1997, J. Virol. 71:1794–1801; Barr, J. N. et al., 1997, J. Virol. 71:8718–8725; Hwang, L. N. et al., 1998, J. Virol. 72:1805–13; Kuo, L. et al., 1996, J. Virol. 70:6143–6150; Rassa, J. C., and G. D. Parks, 1998, Virology, 247: 274–286; Stillman E. A., and M. A. Whitt, 1998, J. Virol. 72: 5565–5572). Certain nucleotide substitutions in these S sequences were shown to decrease transcription initiation efficiency, suggesting that gene expression is also modulated by naturally occurring variations in the viral life cycle. (Kuo, L. et al., 1996, J. Virol. 70:6892–6901; Kuo, L. et al., 1997, J. Virol. 71:4944–4953; Stillman E. A., and M. A. Whitt, 1997, J. Virol. 71:2127–2137). However in the model template systems, all events required early in the natural life cycle like primary transcription is by-passed by the successive and constant supply of trans-acting proteins (Nagai, Y. Paramyxovirus replication and pathogenesis. Reverse genetics transforms understanding. Rev. Medical. Virol. 9(2): 83–99 (1999)). The transcription and replication of minigenomes are uncoupled in these systems. T7 polymerase-expressing vaccinia virus often used to produce tans-acting proteins masks the subtle effects of mutations by, for example, posttranscriptional modifications by capping enzymes encoded by vaccinia viruses. In addition, transfection efficiencies might not be equal throughout the whole experiment (Bukreyev, A. et al., 1996, J. Virol. 70:6634–6641; He, B. et al., 1997, Virology 237:249–260). Namely, effects of nucleotide substitutions in the S sequence on transcription initiation cannot be accurately examined in model template systems. Thus, to comprehensively evaluate the roles of S sequence and E sequence, it was necessary to introduce mutations into the full-length viral genome.

DISCLOSURE OF THE INVENTION

An objective of the present invention is to provide virus vectors of Paramyxoviridae in which the S sequence has been modified so as to modify the expression of genes located downstream thereof, a method for producing the vectors as well as uses thereof.

The present inventors have already succeeded in constructing a system to produce infectious SeV by manipulating their genomes using recombinant DNA techniques. The use of this system enables the regeneration of negative strand RNA viruses based on their corresponding DNA, and to perform reverse genetics of SeV by manipulating various genes of the infectious virus (Kato, A. et al., 1997, EMBO J. 16: 578–587; Kato, A. et al., 1997, J. Virol. 71: 7266–7272; Kuo, L. et al., 1996, J. Virol. 70: 6892–6901; Nagai, Y., 1999, Rev. Medical. Virol. 9: 83–99; Sakaguchi, T. et al., 1997, Virology 235: 360–366). Using this system, the present inventors have attempted to elucidate the significance of heterogeneity found in the S sequences of SeV.

Newly synthesized E sequence and S sequence were ligated to the upstream of the firefly luciferase gene, and this was inserted to the downstream of the noncoding region of the N gene. The S sequences were designed to have same sequence as the four naturally-occurring variations described above. In the constructed recombinant virus, the N mRNA transcription starts by its own S sequence and stops by the synthetic E sequence within the inserted reporter (luciferase) gene. The reporter gene expression, which is driven by each of the different S sequences, was quantitated and compared.

The results obtained here clearly showed that the natural S sequence for the F gene had a significantly lower reinitiation activity than the other three S sequences. When de novo protein synthesis is blocked and genome replication is inhibited, only transcription occurs, and replication does not. By conducting experiments under such conditions, it was confirmed that the reduced luciferase gene expression by the F specific signal was indeed caused primarily at the transcriptional level, and was not a secondary result of replication (FIG. 4). This experiment further showed that the reinitiation activity driven by the S sequence of F gene was approximately one forth of that of the other three.

The reinitiation capacity of different S sequences was then assessed by replacing the natural S sequence of the F gene with that of P/M/HN genes having a higher reinitiation efficiency and by examining replication capability of the recovered virus (SeV/mSf) in cultured cells, in ovo, and in mice. As a result, the inventors found that the replaced S sequence enhances not only F gene expression, but also the expression of downstream genes, again at the transcriptional level (FIGS. 7 and 9).

That is, the present inventors found that the reinitiation activity of S sequence of each gene of viruses belonging to Paramyxoviridae varies from the S sequence. It was also revealed that the substitution of S sequence of a particular gene by another S sequence having a different reinitiation activity enables the modification of expression of not only the gene right after the sequence, but also genes located further downstream of the gene at the transcriptional level, to complete the invention.

This invention relates to virus vectors of Paramyxoviridae in which a S sequence has been modified so as to modify expression levels of genes located downstream of the S sequence, a method for producing such vectors and the use thereof, more specifically to relates to:

(1) a virus vector DNA, wherein the transcription start (S) sequence of at least one gene on the genome of a virus belonging to Paramyxoviridae has been modified so as to modify the expression level of said gene and genes located downstream thereof within the host, (2) the virus vector DNA according to (1), wherein said modification of the transcription start sequence comprises the substitution of said sequence by the transcription start sequence of another gene of a virus belonging to Paramyxoviridae, (3) the virus vector DNA according to (1), wherein said modification of transcription start sequence comprises the substitution of the transcription start sequence of F gene by the transcription start sequence of another gene, (4) the virus vector DNA according to (3), wherein said transcription start sequence of another gene comprises that of a P/M/HN gene type, (5) the virus vector DNA according to (1), wherein said modification of transcription start sequence comprises the substitution of transcription start sequences of N gene and/or P gene by the transcription start sequence of another gene, (6) the virus vector DNA according to (5), wherein said transcription start sequence of another gene comprises the transcription start sequence of F gene, (7) a virus vector DNA according to any one of (1) to (6), wherein said virus vector DNA is defective in F gene and/or HN gene, (8) a virus vector DNA according to any one of (1) to (6), wherein a foreign gene has been inserted into said virus vector DNA, (9) a virus vector of Paramyxoviridae comprising a transcription product from a virus vector DNA according to any one of (1) to (6) within virus particles,

(10) the vector according to (9), wherein said vector is a Sendai virus (SeV) vector,

(11) the vector according to (9), wherein the proliferation capability in the host is elevated compared to that of the wild type virus,

(12) a method for producing a virus vector of Paramyxoviridae, wherein said method comprises the steps of transferring a virus vector DNA according to any one of (1) to (6) into the host, and expressing the virus protein in said host, and

(13) the method according to (12), wherein said virus of Paramyxoviridae used to produce the vector is Sendai virus.

Herein, a "virus vector of Paramyxoviridae" is defined as a vector (or carrier) that is derived from a virus of Paramyxoviridae, and which can transfer a gene to a host cell. The virus vector of Paramyxoviridae of the present invention may be a ribonucleoprotein (RNP) or a virus particle having infectivity. Here, "infectivity" is defined as the ability of the virus vector to transfer, through its cell adhesion and membrane fusion abilities, the virus genome contained in the virus particles to cells, and to express it.

The virus vector of Paramyxoviridae may have a replication capability, or may be a defective vector without the replication capability. Herein, "have a replication capability" is defined as the ability of virus vectors to replicate and produce infective virus particles in host cells infected with the virus vectors.

The virus vector of Paramyxoviridae of this invention can carry a foreign gene in an expressible manner. Such virus vectors can be prepared as recombinant virus vectors of Paramyxoviridae. Herein, a "recombinant" virus vector of Paramyxoviridae is defined as one constructed by genetic engineering, or its amplified products. For instance, recombinant virus vectors of Paramyxoviridae can be generated from a recombinant virus cDNA of Paramyxoviridae.

Herein, a virus of Paramyxoviridae is defined as a virus belonging to the family Paramyxoviridae, or a derivative thereof. The present invention can be applied to, for example, a virus of Paramyxoviridae such as the Sendai virus, Newcastle disease virus, Mumps virus, Measles virus, Respiratory syncytial virus, rinderpest virus, Canine distemper virus, simian parainfluenza virus (SV5), and type I, II, III, and IV human parainfluenza virus. The virus vector and vector DNA of the present invention are preferably derived from a virus of the genus Paramyxovirus (also called Respirovirus) or a derivative thereof. Viruses of the genus Paramyxovirus to which the present invention is applicable include human parainfluenza virus type 1 (HPIV-1), human parainfluenza virus type 3 (HPIV-3), bovine parainfluenza virus type 3 (BPIV-3), Sendai virus (also called murine parainfluenza virus type 1), simian parainfluenza virus type 10 (SPIV-10), and many other viruses of the genus Paramyxovirus. Most preferably, the virus vector and vector DNA of the invention are derived from the Sendai virus. These viruses may be wild-type strains, mutant strains, laboratory-passaged strains, artificially constructed strains, and so on. Incomplete viruses such as the DI particle (Willenbrink W. and Neubert W. J., J. Virol., 1994, 68, 8413–8417), synthesized oligonucleotides, and so on, may also be utilized as material for generating the virus vector of the present invention.

Herein, "virus vector DNA" means DNA comprising a nucleotide sequence encoding the genome of a virus vector. "DNA" herein includes single-stranded DNA and double-stranded DNA. The term "gene" used herein means a genetic substance, which includes nucleic acids such as RNA, DNA, etc. In general, a gene may or may not encode a protein. For example, a gene may be that encoding a functional RNA such as ribozyme, antisense RNA, etc. A gene may have a naturally derived or artificially designed sequence.

Here, the "N, P, M, F, HN, and L genes" of the viruses of Paramyxoviridae represent those encoding the nucleocapsid protein, phosphoprotein, matrix protein, fusion protein, hemagglutinin-neuraminidase, and large protein, respectively. Genes of each virus of the subfamily Paramyxovirinae are described generally as follows. In general, N gene may also be indicated as "NP gene".

| Respirovirus | N | P/C/V | M | F | HN | — | L |
| Rublavirus | N | P/V | M | F | HN | (SH) | L |
| Morbillivirus | N | P/C/V | M | F | H | — | L |

For instance, the accession numbers in the nucleotide sequence database of each gene of the Sendai virus, are M29343, M30202, M30203, M30204, M51331, M55565, M69046, and X17218 for N gene; M30202, M30203, M30204, M55565, M69046, X00583, X17007, and X17008 for P gene; D11446, K02742, M30202, M30203, M30204, M69046, U31956, X00584, X53056 for M gene; D00152, D11446, D17334, D17335, M30202, M30203, M30204, M69046, X00152, and X02131 for F gene; D26475, M12397, M30202, M30203, M30204, M69046, X00586, X02808, X56131 for HN gene; and D00053, M30202, M30203, M30204, M69040, X00587, and X58886 for L gene.

This invention provides virus vectors in which the S sequence of at least one gene on the genome of a virus belonging to Paramyxoviridae has been modified so as to modify the expression levels of the gene and genes located downstream thereof in the host, and also provides DNAs encoding the genome of the virus vectors (called vector DNAs). Virus vectors of this invention are capable of modifying transcription levels of not only a gene right after the S sequence but also gene(s) downstream thereof, by modifying the S sequence.

"Modification of a transcription start (S) sequence" in this invention refers to carrying out the substitution, deletion, addition and/or insertion of one or more nucleotides in the S sequence of a gene on the genome of a virus belonging to Paramyxoviridae or the substitution of the S sequence of a gene by that of another gene of a virus belonging to Paramyxoviridae.

The modification of the S sequence to obtain a sequence having a desired reinitiation activity may be carried out by designing a variety of S sequences, and detecting the reinitiation activity using the luciferase assay and such as described in Example 1 to select a sequence having the desired activity. S sequences may be modified by using known genetic engineering techniques. For example, as described in Example 3, any desired mutation can be introduced into the S sequence of the F gene on the genome of a virus belonging to Paramyxoviridae using site-specific mutagenesis.

Virus vectors of Paramyxoviridae according to this invention include those in which a S sequence has been modified so that the expression level of, for example, the F gene is significantly elevated as compared with the wild type virus. Significant elevation refers to an elevation in expression levels, for example, by 20% or more, preferably 40% or more, more preferably 2-fold or more, even more preferably 3-fold or more as compared with the expression of the wild type F gene. Such vectors can be produced, for example, by substituting the S sequence of the F gene by that of P, M, HN, N or L gene. Virus vectors of Paramyxoviridae according to this invention include those in which the expression level of any of P, M, HN, N or L gene, or any combinations thereof is significantly reduced as compared with the expression of the wild type. Significant reduction means a reduction in expression, for example, by 20% or more, preferably 30% or more, more preferably 40% or more, and even more preferably 60% or more as compared with that of the wild type. Such vectors can be produced, for example, by substituting the S sequence of P, M, HN, N and/or L gene by that of F gene. Especially, virus vectors in which the expression levels of P gene and/or N gene are reduced compared to the wild-type are excellent vectors for gene transfer because of the attenuated cytotoxicity thereof. Expression levels of genes can be measured, for example, through the detection of mRNA (transcription product) or proteins (translation product). The gene expression level is measured preferably under conditions that minimize the effect of virus replication rate. For example, as shown in FIG. 3 of Example 1, gene expression level can be measured under conditions in which only one replication cycle takes place, alternatively, as represented in FIG. 4, by specifically estimating the primary transcription through the detection of RNAs or proteins. These measurements can be carried out, for example, by the methods described in Example 1 or 2.

The present inventors examined the reinitiation activity of 4 different S sequences found in a virus of Paramyxoviridae (Sendai virus), and discovered that the activity was different in each of them and that while the reinitiation activities of the S sequences of L gene (AGGGTGAAT), P/M/HN gene (AGGGTGAAA) and N gene (AGGGTCAAA) showed a high value, the reinitiation activity of the S sequence of F gene (AGGGATAAA) was low. Therefore, when a high reinitiation activity is desired, S sequences of L gene, P/M/HN gene or N gene may be used, while when a low reinitiation activity is preferred, the S sequence of F gene may be used. For example, the substitution of S sequence of F gene by that of P/M/HN gene having a high reinitiation activity can lead to the elevation of transcription levels of F gene and genes located downstream thereof. Furthermore, by substituting the S sequences of N gene and/or P gene by the S sequence of F gene, and such having a lower reinitiation activity, it is possible to reduce virion formation and cytotoxicity of vectors.

There are a variety of advantages of modifying transcription levels of virus genes of Paramyxoviridae. For example, with a virus in which the S sequence of F gene has been substituted by one having a higher reinitiation activity, the viral proliferation capability can be elevated. In addition, by exchanging the S sequence of F gene and that of L gene, it can be expected that only expression levels of F and HN genes would be elevated, leaving the viral proliferation capability unaffected. Furthermore, in the case of a protein whose high expression is undesirable, the expression level of the protein can be restricted by linking the gene thereof to the downstream of the S sequence with a low reinitiation activity, such as that of F gene.

In a viral genome comprising a S sequence modified to have a higher transcription reinitiation activity, the expression level of mRNA encoded by the gene downstream of the modified S sequence is increased compared with the original wild type genome. Accordingly, when a desired foreign gene is located downstream of the modified S sequence, the gene product level is also expected to elevate. Therefore, virus vectors having such genomes are advantageous in that the production efficiency of gene product(s) has been improved. In addition, a virus having such a genome has the advantage of yielding a large amount of viruses in a short time, when collecting recombinant virus particles or virus-like particles as pharmaceutical compositions or vaccines. For example, it has been known that virus particles incubated at 37° C. for 2 days form complexes among them and undergo an aging phenomenon in which their original morphology changes. (Kim, J. et al., Virology 95: 523–535 (1979)). Observation of these under an electron microscope has revealed that the nucleocapsid structure is tightly folded in de novo synthesized viral particles, but unfolds and becomes loose with aging. When utilizing viral particles or virus-like particles as pharmaceutical compositions and vaccines, it is important to obtain homogeneous materials. Therefore, it is necessary to recover viruses from a culture as short as possible. As shown in Examples, the present invention may allow the preparation of modified virus having a titer as high as 100-folds as compared with the wild type virus (FIG. 5).

The virus vector of Paramyxoviridae of the present invention includes, for example, vectors that have the replication capability and those that are capable of autonomous proliferation. In general, the genome of the wild type paramyxovirus contains a short 3' leader region followed by six genes encoding N, P, M, F, HN, and L proteins, and has a short 5' trailer region on the other terminus. The vector of the present invention that is able to replicate autonomously can be obtained by designing a genome having a similar structure to that described above. The virus vector of Paramyxoviridae of the invention may have an altered alignment of virus genes, compared with wild type virus.

The virus vector of Paramyxoviridae of the present invention may be defective in any of the genes that are contained in the wild type virus. For instance, in the case of the reconstitution of the Sendai virus vector, proteins encoded by N, P/C, and L genes are thought to be required in trans, but the genes may not be a component of the virus vector. In one embodiment, an expression vector carrying genes encoding the proteins may be co-transfected into host cells with another expression vector encoding the vector genome to reconstitute a virus vector. Alternatively, an expression vector encoding the virus genome is transfected into host cells carrying genes encoding the proteins, and thus a virus vector can be reconstituted by using the proteins provided by the host cell. The amino acid sequence of these proteins may not be identical to those derived from the original virus as long as it has an equivalent or higher activity in nucleic acid transfer, and may be mutated or substituted with that of a homologous gene of another virus.

Proteins encoded by M, F, and HN genes are thought to be essential for cell-to-cell propagation of almost all viruses of Paramyxoviridae. However, these proteins are not required when the virus vector of Paramyxoviridae is prepared as RNP. If genes M, F, and HN are components of the genome contained in RNP, products of these genes are produced when introduced into host cells, and virus particles having infectivity are generated.

RNP can be introduced into cells as a complex formed with lipofectamine, polycationic liposome, and the like. Specifically, a variety of transfection reagents can be used, for instance, DOTMA (Boehringer), SuperFect (QIAGEN #301305), DOTAP, DOPE, DOSPER (Boehringer #1811169). Chloroquine may be added to prevent degradation in the endosome (Calos M. P., Proc. Natl. Acad. Sci. USA, 1983, 80, 3015). In the case of replicative viruses, the produced viruses can be amplified or passaged by re-infecting into cultured cells, embryonating hen eggs, or animals (e.g. mammalian such as mice).

In addition, the virus vector of Paramyxoviridae of the present invention may be those lacking the M, F, and/or HN genes. These vectors can be reconstituted by providing deficient gene products exogenously. Such vectors can still adhere to host cells and induce cell fusion as the wild type could. However, daughter virus particles do not have the same infectivity as the original ones because the vector genome introduced into cells lacks one of the above genes. Therefore, these vectors can be safer virus vectors that are capable of only a single gene transfer. For instance, genes deleted from the genome may be F and/or HN genes. Virus vectors defective in F gene can be reconstituted by co-transfection of an expression plasmid encoding the genome of a recombinant virus vector of Paramyxoviridae lacking the F gene (containing virus vector DNA), an expression vector for the F protein, and that for N, P/C, and L proteins into host cells (WO00/70055 and WO00/70070). Alternatively, host cells in which the F gene is integrated into the chromosome may be used. The amino acid sequence of these proteins provided exogenously may not be identical to those of the wild type and may be mutated or replaced by a homologous protein of another virus as long as they provide equivalent or higher gene transfer activity.

The envelope proteins of the virus vector of Paramyxoviridae of the present invention may comprise a protein other than the envelope protein of the original vector genome. There is no limitation on such proteins. These may include envelope proteins of other viruses such as the G protein of the vesicular stomatitis virus (VSV-G). Thus, the virus vector of the invention includes a pseudo type virus vector that has an envelope protein derived from a virus different from the original virus.

Any desired foreign gene, which may or may not encode proteins, can be inserted into the virus vector DNAs of this invention. For example, the foreign gene may encode functional RNA such as a ribozyme, anti-sense RNA, and RNAi. Foreign genes can comprise either naturally-occurring or artificially-designed sequences. For example, in gene therapy and such, a gene for treating an objective disorder is inserted into the virus vector DNA. When virus vector DNAs of this invention are used for manufacturing gene therapy vectors, it is desirable to delete F, HN and/or M genes from the virus vector DNAs so as to suppress their toxicity within the host. Furthermore, by substituting the S sequences of N gene and/or P gene by the S sequence having a lower reinitiation activity, it is possible to reduce cytotoxicity of vectors. In the case of introducing a foreign gene into the DNA of virus vector, for example, in that of Sendai virus vector, it is desirable to insert a sequence comprising a multiple of six nucleotides of the foreign gene between the E sequence and S sequence of the virus vector DNA (J. Virol., Vol. 67, No. 8, 1993, p. 4822–4830), etc. A foreign gene can be inserted before and/or after the respective viral genes (N, P, M, F, HN or L genes). E-I-S sequence (transcription end sequence-intervening sequence-transcription start sequence) or portion thereof is appropriately inserted before or after a foreign gene and a unit of E-I-S sequence is located between each gene so as not to interfere with the expression of genes before or after the foreign gene. Expression level of an inserted foreign gene can be regulated by the type of S sequence added to the 5' side (head) of the foreign gene as well as the site of gene insertion and nucleotide sequences before and after the gene. For example, in SeV, it has been known that the nearer the insertion site to the N gene, the higher the expression level of the inserted gene.

Generally, the closer to the 3'-terminus of the negative strand RNA of the virus genome (the closer to N gene in the gene arrangement on the wild type virus genome) the insertion position is, the higher the expression level of the inserted gene will be. To achieve a high expression of a foreign gene, it is preferably inserted into the region near the 3' terminus of the negative stranded genome such as the upstream of the N gene (3'flanking sequence on the minus strand), or between N and P genes. Conversely, the closer to the 5'-terminus of the negative strand RNA (the closer to L gene in the gene arrangement on the wild type virus genome) the insertion position is, the lower the expression level of the inserted gene will be. To reduce the expression of a foreign gene, it may be inserted into the most 5' position on the negative strand, that is, downstream of the L gene in the wild type virus genome (5' flanking region of the L gene on the negative strand) or upstream of the L gene (3' flanking region of L gene on the negative strand) Thus, the insertion position of a foreign gene can be properly adjusted so as to obtain a desired expression level of the gene or optimize the combination of the insert with the virus genes surrounding it. For instance, if the overexpression of a gene introduced by inoculating a high titer virus vector may cause toxicity, it is possible not only to limit the titer of the virus to be inoculated, but also to reduce the expression level from individual virus vectors, for example, by designing the insertion position on the vector as closely to the 5'-terminus of the negative-strand as possible so as to obtain an appropriate therapeutic effect. By combining modifications of S sequences according to this invention, it becomes possible to more precisely regulate gene expression by vectors. To help the easy insertion of a foreign gene, a cloning site may be designed at the position of insertion. For example, the cloning site may be the recognition sequence of restriction enzymes. The restriction sites in the virus vector DNA can be used to insert a foreign gene. The cloning site may be a multicloning site that contains recognition sequences for multiple restriction enzymes. The vector DNA of the present invention may have other foreign genes at positions other than that used for above insertion.

Recombinant SeV vectors comprising a foreign gene can be constructed as follows according to, for example, the description in "Hasan, M. K. et al., J. Gen. Virol. 78: 2813–2820, 1997", "Kato, A. et al., 1997, EMBO J. 16: 578–587", "Kato A. et al., 1999, J. Virol. 73: 9237–9246", "Li, H.-O. et al., 2000, J. Virol. 74: 6564–6569" and "Yu, D. et al., 1997, Genes Cells 2: 457–466".

First, a DNA sample comprising the cDNA nucleotide sequence of a desired foreign gene is prepared. It is preferable that the DNA sample can be electrophoretically identified as a single plasmid at concentrations of 25 ng/μl or more. Below, a case where a foreign gene is inserted to DNA encoding viral genome utilizing NotI site will be described as an example. When NotI recognition site is included in the objective cDNA nucleotide sequence, it is preferable to delete the NotI site beforehand by modifying the nucleotide sequence using site-specific mutagenesis and such method so as not to alter the amino acid sequence encoded by the cDNA. From this DNA sample, the desired gene fragment is amplified and recovered by PCR. To have NotI sites on the both ends of amplified DNA fragment and further add a copy of E-I-S sequence of SeV to one end, a forward side synthetic DNA sequence (sense strand) and reverse side synthetic DNA sequence (antisense strand) are prepared as a pair of primers containing NotI restriction enzyme cleavage site sequence, E-I-S sequence and a partial sequence of the objective gene.

For example, to secure cleavage by NotI, the forward side synthetic DNA sequence is arranged in a form in which any two or more nucleotides (preferably 4 nucleotides excluding GCG and GCC, sequences originating in NotI recognition site, more preferably ACTT) are selected on the 5'-side of the synthetic DNA, NotI recognition site "gcggccgc" is added to its 3'-side, and to the 3'-side thereof, any desired 9 nucleotides or nucleotides of 9 plus a multiple of 6 nucleotides are added as the spacer sequence, and to the 3'-side thereof, about 25 nucleotide-equivalent ORF including the initiation codon ATG of the desired cDNA is added. It is preferable to select about 25 nucleotides from the desired cDNA as the forward side synthetic DNA sequence so as to have G or C as the final nucleotide on its 3'-end.

In the reverse side synthetic DNA sequence, any two or more nucleotides (preferably 4 nucleotides excluding GCG and GCC, sequences originating in the NotI recognition site, more preferably ACTT) are selected from the 5'-side of the synthetic DNA, NotI recognition site "gcggccgc" is added to its 3'-side, and to its further 3'-side, an oligo DNA is added as the insertion fragment to adjust the length. This oligo DNA is designed so that the total nucleotide number including the NotI recognition site "gcggccgc", complementary sequence of cDNA and EIS nucleotide sequence of SeV genome originating in the virus described below becomes a multiple of six (so-called "rule of six"; Kolakofski, D. et al., J. Virol. 72: 891–899, 1998; Calain, P. and Roux, L., J. Virol. 67:4822–4830, 1993; Calain, P. and Roux, L., J. Virol. 67: 4822–4830, 1993). Further to the 3'-side of inserted fragment, a sequence complementary to S sequence of Sendai virus, preferably 5'-CTTTCACCCT-3' (SEQ ID NO: 1), I sequence, preferably 5'-AAG-3', and a sequence complementary to E sequence, preferably 5'-TTTTTCTTAC-TACGG-3' (SEQ ID NO: 2), is added, and further to the 3'-side thereof, about 25 nucleotide-equivalent complementary sequence counted in the reverse direction from the termination codon of the desired cDNA sequence the length of which is adjusted to have G or C as the final nucleotide, is selected and added as the 3'-end of the reverse side synthetic DNA.

PCR can be done according to the usual method with, for example, ExTaq polymerase (Takara Shuzo). Preferably, PCR is performed using Vent polymerase (NEB), and desired fragments thus amplified are digested with NotI, then inserted to NotI site of the plasmid vector pBluescript. Nucleotide sequences of PCR products thus obtained are confirmed with a sequencer to select a plasmid having the right sequence. The inserted fragment is excised from the plasmid using NotI, and cloned to the NotI site of the plasmid carrying the genomic cDNA. Alternatively, it is also possible to obtain the recombinant Sendai virus cDNA by directly inserting the fragment to the NotI site without the mediation of the plasmid vector pBluescript.

By transferring a virus vector DNA of this invention into host cells to express it therein, it is possible to prepare a virus vector comprising a transcription product from the virus vector DNA within virus particles. Specifically, a virus vector DNA of this invention may be transferred into host cells to express a viral protein within the host cells. Virus vector DNA encodes negative-strand single-stranded RNA (negative-strand) or complementary strand thereof (positive-strand). For example, DNA encoding negative-strand single-stranded RNA or complementary strand thereof is linked downstream of T7 promoter to be transcribed to RNA by T7 RNA polymerase. Desired promoters can be used except those including the recognition sequence of T7 polymerase. Alternatively, RNA transcribed in vitro may be transfected into helper cells. Vector DNAs may be cloned into plasmids to amplify in E. coli. Although the strand to be transcribed inside cells may be either positive or negative-strand, reconstitution efficiency is preferably improved by arranging so as to transcribe the positive strand. Transfer of the virus vector DNA into host cells may precede the expression of viral proteins inside the host cells or vice versa, or these processes may be simultaneously carried out. Viral proteins can be expressed inside host cells by transferring, for example, expression vectors encoding the viral proteins to the host. When a virus vector DNA is made defective in F, HN and/or M genes, infectious virus particles are not formed with such a defective vector. However, it is possible to form infectious virus particles by separately transferring these defective genes, genes encoding other viral envelope proteins, and such, to host cells and expressing them therein.

Methods for transferring virus vector DNA into cells include the following: 1) the method of preparing DNA precipitates that can be taken up by objective cells; 2) the method of preparing a DNA comprising complex which is suitable for being taken up by objective cells and which is also not very cytotoxic and has a positive charge, and 3) the method of instantaneously boring on the objective cellular membrane pores wide enough to allow DNA molecules to pass through by electric pulse.

In Method 2), a variety of transfection reagents can be utilized, examples being DOTMA (Boehringer), SuperFect (QIAGEN #301305), DOTAP, DOPE, DOSPER (Boehringer #1811169), etc. An example of Method 1) is a transfection method using calcium phosphate, in which DNA that entered cells are incorporated into phagosomes, and a sufficient amount is incorporated into the nuclei as well (Graham, F. L. and Van Der Eb, AJ., 1973, Virology 52: 456; Wigler, M. and Silverstein, S., 1977, Cell 11: 223). Chen and Okayama have investigated the optimization of the transfer technique, reporting that suitable DNA precipitates can be obtained under the conditions where 1) cells are incubated with DNA in an atmosphere of 2 to 4% $CO_2$ at 35° C. for 15 to 24 h, 2) circular DNA with a higher precipitate-forming activity than linear DNA is used, and 3) DNA concentration in the precipitate mixture is 20 to 30 μg/ml (Chen, C. and Okayama, H., 1987, Mol. Cell. Biol. 7: 2745). Method 2) is suitable for a transient transfection. An old method is known in the art in which a DEAE-dextran (Sigma #D-9885, M.W. $5×10^5$) mixture is prepared in a desired DNA concentration ratio to perform the transfection. Since most of the complexes are decomposed inside endosomes, chloroquine may be added to enhance transfection effects (Calos, M. P., 1983, Proc. Natl. Acad. Sci. USA 80: 3015). Method 3) is referred to as electroporation, and is more versatile compared to methods 1) and 2) because it doesn't have cell selectivity. Method 3) is the to be efficient under optimal conditions for pulse electric current duration, pulse shape, electric field potency (gap between electrodes, voltage), conductivity of buffers, DNA concentration, and cell density.

Among the above-described three categories, transfection reagents (method 2)) are suitable in this invention, because method 2) is easily operable, and facilitates the examining of many test samples using a large amount of cells. Preferably, SuperFect (QIAGEN #301305) or DOSPER (Boehringer #1811169) is used.

Reconstitution of a virus from cDNA can be performed according to the known methods (WO97/16539; WO97/16538; Durbin A. P. et al., Virol., 1997, 235, 323–332; Whelan S. P. et al., Proc. Natl. Acad. Sci. USA, 1995, 92, 8388–8392; Schnell M. J. et al., EMBO J., 1994, 13, 4195–4203; Radecke F. et al., EMBO J., 1995, 14, 5773–5784; Lawson N. D. et al., Proc. Natl. Acad. Sci. USA, 1995, 92, 4477–4481; Garcin D. et al., EMBO J., 1995, 14, 6087–6094; Kato A. et al., Genes Cells, 1996, 1, 569–579; Baron M. D. and Barrett T., J. Virol., 1997, 71, 1265–1271; Bridgen A. and Elliott R. M., Proc. Natl. Acad. Sci. USA, 1996, 93, 15400–15404). These methods enable the reconstitution of any desired virus vectors of Paramyxoviridae including the parainfluenza virus, measles virus, rinderpest virus, and Sendai virus vectors from DNA.

For example, simian kidney-derived LLC-MK2 cells are cultured in 24-well to 6-well plastic culture plates or 100 mm diameter culture dish using a minimum essential medium (MEM) containing 10% fetal calf serum (FCS) and antibiotics (100 units/ml penicillin G and 100 μg/ml streptomycin) to 70 to 80% confluency, and infected, for example, with recombinant vaccinia virus vTF7-3 expressing T7 polymerase at 2 PFU/cell. This virus can be inactivated by a UV irradiation treatment for 20 min in the presence of 1 μg/ml psoralen (Fuerst, T. R. et al., Proc. Natl. Acad. Sci. USA 83: 8122–8126, 1986; Kato, A. et al., Genes Cells 1: 569–579, 1996). Amount of psoralen added and UV irradiation time can be appropriately adjusted. One hour after the virus adsorption, the cells are transfected with 2 to 60 μg, more preferably 3 to 5 μg, of the above-described recombinant SeV cDNA by the lipofection method and such using plasmids (24 to 0.5 μg of pGEM-N, 12 to 0.25 μg of pGEM-P and 24 to 0.5 μg of pGEM-L, more preferably 1 μg of pGEM-N, 0.5 μg of pGEM-P and 1 μg of pGEM-L) (Kato, A. et al., Genes Cells 1:569–579, 1996) expressing trans-acting viral proteins required for the production of full-length SeV genome together with SuperFect (QIAGEN). The transfected cells are cultured in a serum-free MEM containing 100 μg/ml each of rifampicin (Sigma) and cytosine arabinoside (AraC) if desired, more preferably only containing 40 μg/ml of cytosine arabinoside (AraC) (Sigma), and concentrations of reagents are set at optima so as to minimize cytotoxicity due to the vaccinia virus and maximize the reconstitution rate of the virus (Kato, A. et al., 1996, Genes Cells 1, 569–579). After culturing for about 48 to 72 h following the transfection, the cells are reconstituted, disrupted by repeating three cycles of freezing and thawing, transfected to LLCMK2 cells, and cultured, or inoculated into embryonated chicken eggs. After culturing the cells for 3 to 7 days, the culture solution is collected. Virus vectors defective in the envelope protein-encoding gene without replication capability can be reconstituted by using LLCMK2 cells expressing envelope proteins for transfection, or transfecting together with an envelope-expressing plasmid. Defective virus vectors can be amplified by culturing the transfected cells overlaid on LLCMK2 cells expressing envelope proteins (WO00/70055 and WO00/70070). Virus titer contained in the culture supernatant can be determined by measuring the hemagglutination activity (HA), which can be assayed by "endo-point dilution method" (Kato, A. et al., 1996, Genes Cells 1, 569–579). Virus stock thus obtained can be stored at −80° C. without the aging.

The type of host cells used for virus reconstitution is not particularly limited, so long as virus vector can be reconstituted therein. For example, in the reconstitution of SeV vector and such, culture cells such as simian kidney-derived CVI cells and LLCMK2 cells, hamster kidney-derived BHK cells, human-derived cells, and so on can be used. To obtain SeV vector in a large quantity, the vector can be amplified by infecting virus vector obtained from the above-described host cells into embryonated hen eggs. Methods for manufacturing virus using hen eggs have been already developed (Nakanishi, et al. (eds.), 1993, "Shinkei-kagaku Kenkyu-no Sentan-gijutu Protocol III (High Technology Protocol III of Neuroscience Research), Molecular Neurocyte Physiology, Koseisha, Osaka, pp. 153–172). Specifically, for example, fertilized eggs are placed in an incubator and incubated for 9 to 12 days at 37 to 38° C. to grow embryos. Virus vector is inoculated into allantoic cavity of eggs, and cultured for several days to proliferate the virus. Conditions such as culture duration may be varied depending on the type of recombinant virus used. Subsequently, allantoic fluid comprising the virus is recovered. Separation and purification of SeV vector can be performed according to the standard methods (Tashiro, M., "Virus Experiment Protocols", Nagai and Ishihama (eds.) Medicalview, pp. 68–73 (1995)).

Also, the virus vector of the invention may have on the surface of its envelope adhesion molecules, ligands, receptors, or fragments thereof so as to adhere to specific cells. If vectors comprising a chimeric protein having these proteins in its extracellular domain and a polypeptide derived from the virus envelope protein in its intracellular domain, and such are prepared, it enables the production of a vector targeting a particular tissue. These factors may be encoded by the virus genome itself, or supplied at the time of virus reconstitution through expression of genes other than virus genome (for example, another expression vector or host cell chromosome).

The virus genes contained in the recombinant virus vector may be modified, for example, to reduce antigenicity or enhance RNA transcription efficiency or replication efficiency. Specifically, it is possible to modify at least one of the N, P/C, and L genes, which are genes of replication factors, to enhance transcription or replication. It is also possible to modify the HN protein, a structural protein having hemagglutinin activity and neuraminidase activity, to enhance the virus stability in blood by weakening the former activity and to regulate infectivity by modifying the latter activity. It is also possible to modify the F protein, which is implicated in membrane fusion, to regulate the fusion ability of membrane-fused liposomes. Furthermore, it is possible to generate a virus vector of Paramyxoviridae that is engineered to have weak antigenicity through analyzing the antigen presenting epitopes and such of possible antigenic molecules on the cell surface such as the F protein and HN protein.

In addition, virus vectors of Paramyxoviridae whose accessory gene is defective can be used as the virus vector of the present invention. For example, by knocking out V gene, one of the accessory genes of SeV, pathogenicity of SeV to hosts such as mice markedly decreases without damages to the expression and replication of genes in cultured cells (Kato, A. et al., 1997, J. Virol. 71: 7266–7272; Kato, A. et al., 1997). Such attenuated vectors are particularly preferable as virus vectors for in vivo or ex vivo gene transfer.

In preparing defective virus vectors, two different virus vectors defective in a different envelope gene may be transfected into the same cell. In this case, each defective envelope protein is supplied through expression from the other vector, and this mutual complementation permits the generation of infective virus particles, which can replicate and propagate. Thus, two or more of the virus vectors of the present invention may be simultaneously inoculated in a combination that complement each other, thereby producing a mixture of each envelope defective virus vector at a low cost and in a large scale. Because such viruses lacking an envelope gene have a smaller genome, they can allow the insertion of a long foreign gene. In addition, it is difficult for these viruses, which are intrinsically non-infective, to keep the status of co-infection after being diluted outside cells, -and thus they are sterilized and less harmful to the environment.

Reconstituted paramyxovirus can be purified so as to be substantially pure. Purification can be performed by known purification and separation methods including filtration, centrifugation, column chromatographic purification, and such or by combination thereof. The term "substantially pure" used herein means that virus occupies the main ratio as a component of the sample in which the virus exists. Typically, substantially pure virus vectors can be detected by confirming that the ratio of the virus-derived proteins to the total proteins including in the sample occupies 50% or more, preferably 70% or more, more preferably 80% or more, and even more preferably 90% or more. Specifically, paramyxovirus can be purified, for example, by a method in which cellulose sulfate ester or crosslinked polysaccharide sulfate ester is used (Examined Published Japanese Patent Application (JP-B) No. Sho 62-30752; JP-B Sho 62-33879; JP-B Sho 62-30753), a method in which adsorption to fucose sulfate-containing polysaccharide and/or a decomposition product thereof is used (WO97/32010), etc.

In applying a virus vector thus obtained to gene therapy, it is possible to express a foreign gene with which treatment effects are expected, or an endogenous gene the supply of which is insufficient in a patient's body, by either direct or indirect (ex vivo) administration of the virus vector. There is no particular limitation in the type of the foreign gene, which may be, in addition to nucleic acids encoding proteins, nucleic acids that do not encode a protein such as an antisense or ribozyme. There is no particular limitation on the type of proteins encoded by foreign genes, and examples of natural proteins are hormones, cytokines, growth factors, receptors, enzymes, peptides, etc. These proteins can be secretory proteins, membrane proteins, cytoplasmic proteins, nucleoproteins, etc. Examples of artificial proteins are fusion proteins such as chimeric toxins, dominant negative proteins (including soluble molecules of receptors or membrane-binding dominant negative receptors), deletion-type cell adhesion molecules and cell surface molecules. These proteins may be those to whom a secretion signal, membrane localization signal, nuclear localization signal, etc., has been added. It is also possible to suppress functions of undesirable genes expressed in target cells by expressing an antisense RNA molecule or RNA-cleaving ribozyme, etc. Objects of gene therapy to which administratable vectors of this invention can be applied may include cancer therapy achieved by expressing, for example, a gene causing cell death such as a suicide gene (HSV tk, etc.) which exhibits toxicity to infected cells. Another example is preventive therapy for coronary artery restenosis due to arterial sclerosis. In addition, the application of a virus vector of this invention in gene therapy that aims at maintaining cell survival may include the supplementation of gene products of genes such as adenosine deaminase gene (ADA), cystic fibrosis transmembrane conductance regulator gene (CFTR), and so on, which have been known to be deleted or defective in monogenic disorders, etc.

Regardless of whether the aim of gene therapy is to cause cell death or maintain cell survival, vectors of this invention comprising RNA as the genome can be applied to a wide range of disorders, because they are not converted into DNA during transcription and self-replication processes thereof, and also because they are unlikely to be incorporated into chromosomes of reproductive cells, and such, to affect genes of the succeeding generations. That is, vectors of this invention can be applied to disorders caused by many genes, such as hypertension, diabetes mellitus, asthma, ischemic heart disease, and so on, treatments and prevention for many healthy subjects, such as vaccines, and vaccination to prevent various infectious diseases such as AIDS, malaria, influenza, etc. Furthermore, the vectors of the present invention are highly safe since homologous recombination has not been observed. Thus, replication-incompetent viral constructs grown in complementing cells should be free of a contaminating virus generated by a recombination event. These properties are principally shared by other members of Mononegavirales and weigh heavily in their favour in terms of both utility and safety.

The virus vector of the present invention can be made as a composition together with a desired, pharmaceutically acceptable carrier. Herein, a "pharmaceutically acceptable carrier" is defined as those materials that can be administered with a vector, but does not inhibit gene transfer by the vector. For instance, the virus vector of this invention may be appropriately diluted with physiological saline, phosphate buffered saline (PBS), and so on to make a composition. If the virus vector of the invention is propagated in hen eggs, and such, the composition may contain an allantoic fluid. Also, the composition may contain carriers such as deionized water or a 5% dextrose aqueous solution. It may further contain stabilizers, antibiotics, or the like. Compositions containing virus vectors of the present invention are useful as reagents and pharmaceuticals. Dose of the vectors may vary depending on a disease, body weight, age, sex, symptom, administration purpose, form of a composition to be inoculated, administration method, gene to be introduced, and so on, but it can be properly determined by one skilled in the art. It is preferable to inoculate, with pharmaceutically acceptable carriers, the vectors whose concentration is within the range of preferably about $10^5$ pfu/ml to about $10^{11}$ pfu/ml, more preferably about $10^7$ pfu/ml to about $10^9$ pfu/ml, and most preferably about $1\times10^8$ pfu/ml to about $5\times10^8$ pfu/ml. The virus vector-containing composition of the invention can be administered to any mammals including humans, monkeys, mice, rats, rabbits, sheep, cattle, dogs, etc.

BRIEF DESCRIPTION OF THE DRAWINGS

FIG. 2 shows gene construction of SeV.

FIG. 16 shows the hemagglutination activity (HA activity) of samples taken periodically from the culture supernatant (changing the medium to a fresh one at the same time) of LLC-MK2 cells infected with SeV18+/ΔF-GFP, SeV18+/S(N/F)ΔF-GFP, SeV18+/S(P/F)ΔF-GFP or SeV18+/S(P/F)(N/F)ΔF-GFP at an m.o.i. of 1 or 3, and cultured at 37° C.

BEST MODE FOR CARRYING OUT THE INVENTION

The present invention will be explained in detail below with reference to examples, but it is not to be construed as being limited thereto. Any literatures cited herein are incorporated by reference.

EXAMPLE 1

Construction of Recombinant Viruses and Luciferase Assay

The nine nucleotides of the SeV E sequence are conserved exactly among all genes. On the other hand, there are minor differences in the nine nucleotides of S sequence. While S sequence of three (P, M and HN) of six genes are 3'-UC-CCACUUU-5', that of N, F and L gene are 3'-UC-CCAgUUU-5', 3'-UCCCuaUUU-5', and 3'-UCCCACUUa-5', respectively (FIG. 2). These minor differences are completely conserved in all strains of SeV regardless of the passage history, virulence and isolation strategy. To examine the role of these minor differences of S, the inventors created the four recombinant SeVs named SeV/SpLuc, SeV/SnLuc, SeV/SfLuc and SeV/SlLuc expressing the luciferase under the control of synthetic S sequence.

1-1. Creation of an Insertion Site After the N ORF

Figure 1:
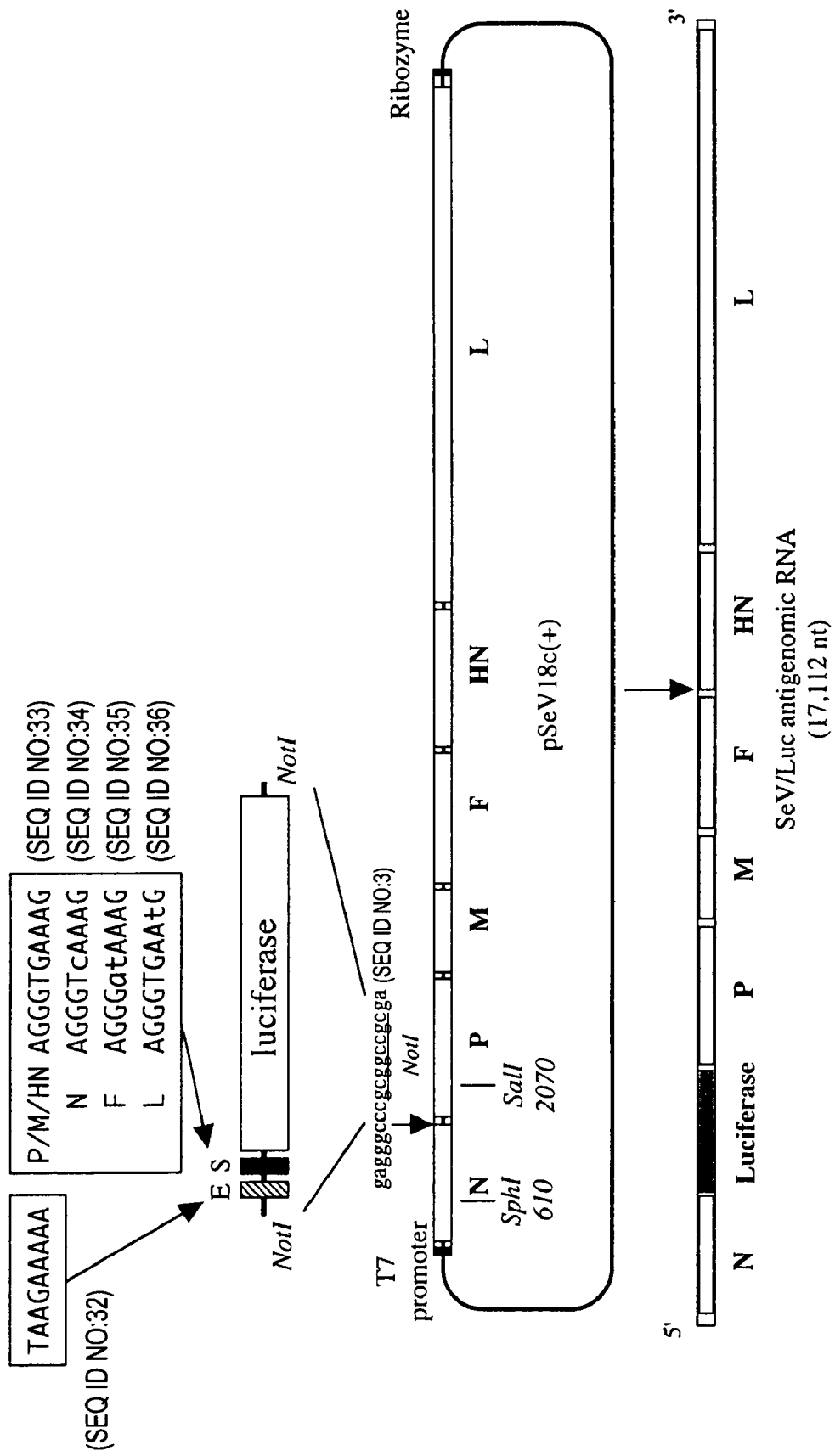
FIG. 1 shows construction of the plasmid pSeV18c(+) and insertion of the luciferase gene into the downstream region of N ORF. An 18 nucleotide-fragment designed to contain a NotI site was inserted between 1698 and 1699 nucleotides from the 3' end of SeV genome in pSeV(+) by site-directed mutagenesis (Shioda, T. et al., 1983, Nucleic Acids Res. 11:7317–7330). The resulting plasmid encoding the SeV antigenome with the 18 nucleotides-insertion was named pSeV18c(+). The ORF of the luciferase gene was PCR-amplified with 4 sets of NotI-tagged primers (ESn/NotLr, ESp/NotLr, ESf/NotLr and ESl/NotLr) from the template plasmid, pHvLuc-RT4 (Kato, A. et al., 1996, Genes to Cells 1: 569–579) to generate the fragments containing each of the different natural S sequences placed at the head of the luciferase gene. These amplified fragments were digested with NotI, and introduced into the same site of pSeV18c (+). The resulting plasmids, named pSeV(+)SnLuc, pSeV(+)SpLuc, pSeV(+)SfLuc and pSeV(+)SlLuc, were used to recover the recombinant SeV/SnLuc, SeV/SpLuc, SeV/SfLuc and SeV/SlLuc, respectively.

The plasmid pSeV(+) contained the cDNA copy of full-length SeV antigenome (Kato, A. et al., 1996, Genes to Cells 1: 569–579) was used as the starting material for plasmid construction. In order to insert a luciferase gene having synthetic E sequence and S sequence, a unique NotI site was created at downstream of N ORF in N gene. Eighteen nucleotides (5'-gagggcccgcggccgcga-3'/SEQ ID NO: 3) containing NotI restriction site was inserted between 1698 and 1699 nucleotides from the 3' end of SeV genome which was located within the 5' non-coding (in negative sense) region of N gene as shown in FIG. 1 (Shioda, T. et al., 1983, Nucleic Acids Res. 11:7317–7330). For the insertion, the inventors used site-directed mutagenesis by a PCR-mediated overlap primer extension method (Ho, S. N. et al., 1989, Gene 77:51–59) essentially according to the previous paper (Hasan, M. K. et al., 1997, J. Gen. Virol. 78:2813–2820). Specifically, two primers (NmF; 5'-gagggcccgcggccgcga$^{1699}$TACGAGGCTTCAAGGTACTT$^{1718}$-3'/SEQ ID NO: 4 and NmR; 5'-tcgcggccgcgggccctc$^{1698}$TGATCCTAGATTCC TCCTAC$^{1670}$-3'/SEQ ID NO: 5) with overlapping 18 nucleotides ends, and two outer primers (OP1, 5'-$^{61}$CAAAG-TATCCACCACCCTGAGGAGCAGGTTCCA-GACCCTTTGCTTTGC$^{105}$-3'/SEQ ID NO: 6 and OP2, 5'-$^{2467}$TTAAGTTGGTVAGTGACTC$^{2449}$-3'/SEQ ID NO: 7) were synthesized. First PCRs were performed with the OP1/NmF primer pairs and the OP2/NmF primer pairs using the pSeV(+) as a template to gave rise to 1.6 Kb- and 0.8 Kb-fragments, respectively. Second PCR was then performed with OP1/OP2 primer pairs using the purified 1.6 Kb- and 0.8 Kb-fragments as the template to generate the single 2.4 Kb-fragment with the 18 nucleotides. The 2.4 Kb-fragment was purified and digested with SphI and SalI. The plasmid pSeV(+) was cut at the positions of 610 and 2070 on the SeV genome by these enzymes. The sequence of the resulting 1.47 Kb-fragment was verified by sequencing using an AFLII automated DNA sequencer (Pharmacia, Uppsala) and replaced with the corresponding fragment of parental pSeV(+), thus generating pSeV18c(+) containing an unique (sole) restriction site after the N ORF.

Like parental plasmid pSeV(+), recombinant viruses can be reconstituted from thus obtained plasmid having an 18-nucleotied insert containing an NotI restriction site. The infectivity and replication capability of the generated viruses were also similar to those of the parental pSeV(+).

1-2. Insertion of Luciferase Gene Regulated by Various S Sequences into Vector

The luciferase gene from the firefly (*Photinus pyralis*) derived from the pHVlucRT4(−) (Kato, A. et al., 1996, Genes to Cells 1: 569–579) was amplified by PCR with the following four primer pairs corresponding to the four different S sequences; four forward primers (ESp; 5'-TTgcggccgcGTAAGAAAAACTTAGGGTGAAAGTTCACTT CACGATGGAAGACGGCAAAAACAT-3'/SEQ ID NO: 8, ESn; 5'-TTgcggccgcGTAAGAAAAACTTAGGGTcAAA GTTCACTTCACGATGGAAGACGGCAAAAA CAT-3'/ SEQ ID NO: 9, ESf; 5'-TTgcggccgcGTAAGAAAAACTT AGGGatAAAGTTCACTTCACGATGGAAGACGGCAA AAA CAT-3'/SEQ ID NO: 10, and ESl; 5'-TTgcggccgcG TAAGAAAAACTTAGGGTGAAtGTTCACTTCACGAT GGAAGACGGCAAAAACAT-3'/SEQ ID NO: 11) and one common reverse primer (NotLr; 5'-TCgcggccgcTATTA-CAATTTGGACTTTCCG-3'/SEQ ID NO: 12). Underlined are a new set of SeV E sequence and S sequence connected with the conserved intergenic trinucleotide and the lower case letters without underline represent the NotI restriction site. The lower case letters with underline represent each of the unique nucleotides in the primers. The 1.7 Kb-fragments amplified with the primer pairs of ESp/NotLr, ESn/NotLr, ESf/NotLr and ESl/NotLr were purified, digested with NotI and directly introduced into the NotI site of pSeV18c(+) (FIG. 1) The final constructs were named pSeV(+)SpLuc, pSeV(+)SnLuc, pSeV(+)SfLuc and pSeV(+)SlLuc, respectively, according to the S sequence used.

1-3. Virus Recovery from cDNAs

Viruses were recovered from cDNAs essentially according to the previously described procedures (Kato, A. et al., 1996, Genes to Cells 1: 569–579). Specifically, 2×10$^6$ of LLCMK2 cells in 6 cm diameter plate were infected with vaccinia virus (VV), vTF7-3, a gift of Dr. B. Moss (Fuerst, T. R. et al., 1986, Proc. Natl. Acad. Sci. USA 83:8122–8126), at moi of 2 PFU/cell. Then, 10 μg of the parental or mutated pSeV(+) and the plasmids encoding trans-acting proteins, pGEM-N (4 μg), pGEM-P (2 μg) and pGEM-L (4 μg) (Kato, A. et al., 1996, Genes to Cells 1: 569–579) were transfected simultaneously with the aid of the lipofection reagent DOTAP (Boehringer-Mannheim, Mannheim). The cells were maintained in serum free MEM in the presence of 40 μg/ml araC (1-β-D-arabinofuranosyl-cytosine) and 100 μg/ml rifampicin to minimize VV cytopathogenicity and thereby maximize the recovery rate. Forty hours after transfection, cells were harvested, disrupted by three cycles of freezing and thawing and inoculated into 10-day-old embryonated hen eggs. After 3 days of incubation, the allantoic fluid was harvested. The titers of recovered viruses were expressed in hemagglutination units (HAU) and PFU/ml as described previously (Kato, A. et al., 1996, Genes to Cells 1: 569–579). The helper VV contaminating the allantoic fluid of the eggs, containing 10$^8$ to 10$^9$ pfu/ml of the recovered SeVs, was eliminated by the second propagation in eggs at a dilution of 10$^{-7}$. This second passaged fluids, stored at −80° C., were used as the seed virus for all the experiments.

1-4. Cell Cultures and Virus Infection

Monkey kidney-derived cell lines LLCMK2 and CV1, were grown in minimal essential medium (MEM) supplemented with 10% fetal bovine serum at 37° C. Monolayer cultures of these cells were infected with the mutant viruses recovered from cDNAs at an input moi of 10 PFU/cell, and maintained in serum-free MEM. The wild-type SeV (Z strain) recovered from the cDNA (Kato, A. et al., 1996, Genes to Cells 1: 569–579) was used as a control.

It was found that the four recombinant viruses had replicated more slowly than the wild type in CV1 cells probably because of accommodating an extra gene as long as 1,728 nucleotides (Hasan, M. K. et al., 1997, J. Gen. Virol. 78:2813–2820). Among the four recombinants, SeV/SfLuc has replicated most slowly.

1-5. Luciferase Assay

Luciferase activities expressed from the recombinant SeVs were compared with each other. The expression of luciferase activity from SeV was studied in 5×10$^5$ cells/well of CV1 cells in 6-well plates at various input multiplicities from 1 to 300 pfu per cell. Under the single-cycle growth conditions, cells were harvested at 0, 6, 14, 20 and 26 hrs post infection (p.i.). The luciferase activity of harvested cells was measured by a luciferase assay kit (Promega, Madison) with a luminometer (Luminos CT-9000D, Dia-Iatron, Tokyo) as described before (Hasan, M. K. et al., 1997, J. Gen. Virol. 78:2813–2820; Kato, A. et al., 1996, Genes to Cells 1: 569–579).

Figure 3:
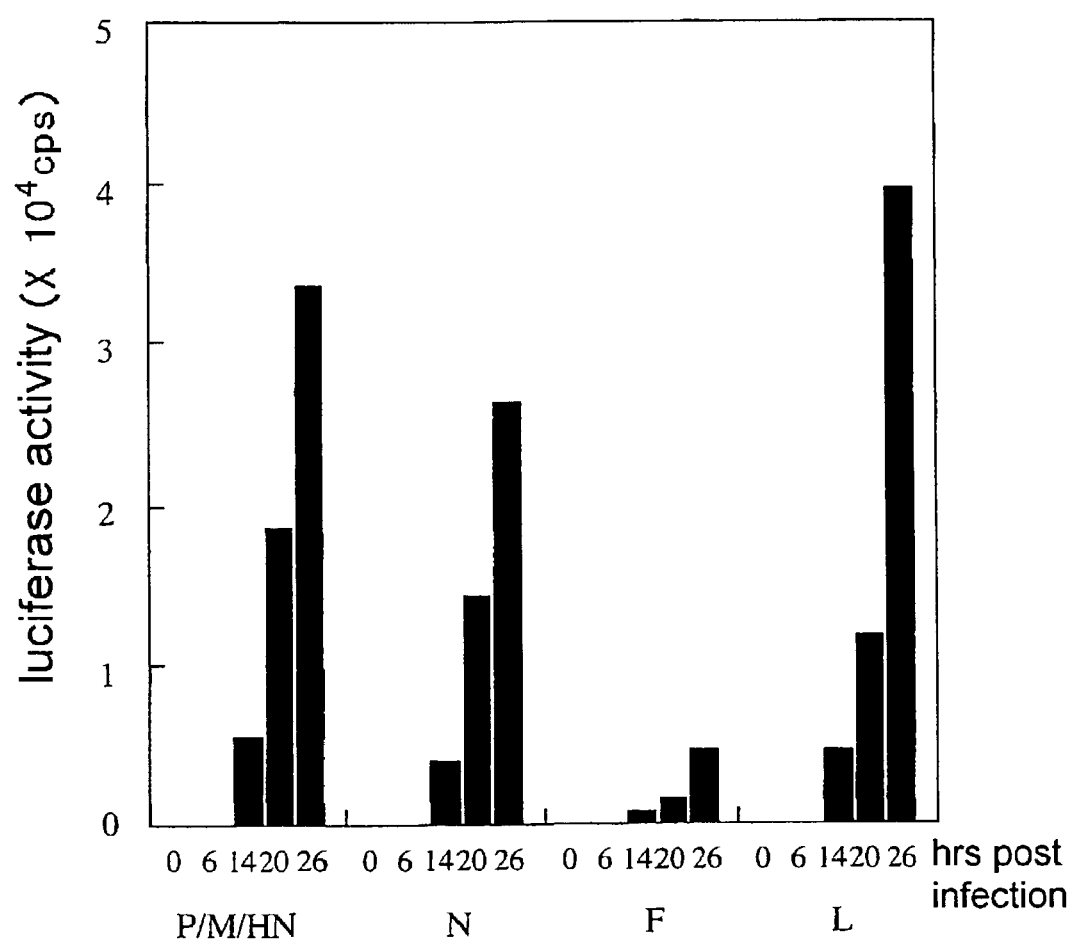
FIG. 3 shows luciferase expression of SeV/SpLuc, SeV/SnLuc, SeV/SfLuc and SeV/SlLuc. The recombinant viruses were inoculated to CV1 cells at an moi of 10 (pfu/cell). The luciferase activities were measured at the times (hr) indicated.

The luciferase activities expressed from SeVs increased in accordance with the infection time and infective dose in all recombinants. FIG. 3 shows changes of luciferase activity when the viruses were infected at moi 10 to CV1 cells.

These cells were collected, and Northern hybridization was performed by using luciferase cDNA as probe. Northern hybridization was conducted as follows. RNAs were extracted from the cells using TRIzol (Gibco BRL, N.Y.). The RNAs were ethanol precipitated, dissolved in formamide/formaldehyde solution, then electorphoresed in 0.9% agarose-formamide/MOPS gels, and capillary transferred onto Hibond-N filters (Amersham, Buckighamshire). The filters were probed with $^{32}$P-labeled probes made by the multi-prime labeling kit (Amersham, Buckighamshire). For the luciferase probe, the NarI/HincII (1270 bp) fragment was purified from pHvlucRT4 (Kato, A. et al., 1996, Genes to Cells 1: 569–579). It was verified that the luciferase mRNAs are synthesized as monocistronoc mRNAs.

These data unequivocally demonstrated that the synthetic E sequence and S sequence inserted just before the luciferase ORF are correctly recognized by the viral RNA polymerase. However, there were differences in luciferase activities in the cells infected with these four viruses even under same condition. The highest activity was obtained with SeV/SlLuc and the lowest activity with SeV/SfLuc at 26 hr p.i. (FIG. 3). SeV/SpLuc and SeV/SnLuc were slightly lower than SeV/SlLuc at 26 hr p.i. However, this was not seen at 14 and 20 hrs p.i. Thus, the reinitiation capacities of Sp, Sn and Sl were regarded to be comparable.

EXAMPLE 2

Comparison of Primary Transcription Amounts from Recombinant Viruses

To see whether or not the differences of the expression amounts among four recombinant SeVs observed in Example 1 were primarily brought about at the level of transcription, but not in the replication process, CV1 cells infected with the recombinants were incubated in the presence of cycloheximide, which inhibits protein synthesis and hence, blocks viral replication requiring de novo viral protein synthesis. Under these conditions, only the viral primary transcription catalyzed by the virion-associated RNA polymerase is allowed.

Figure 4:
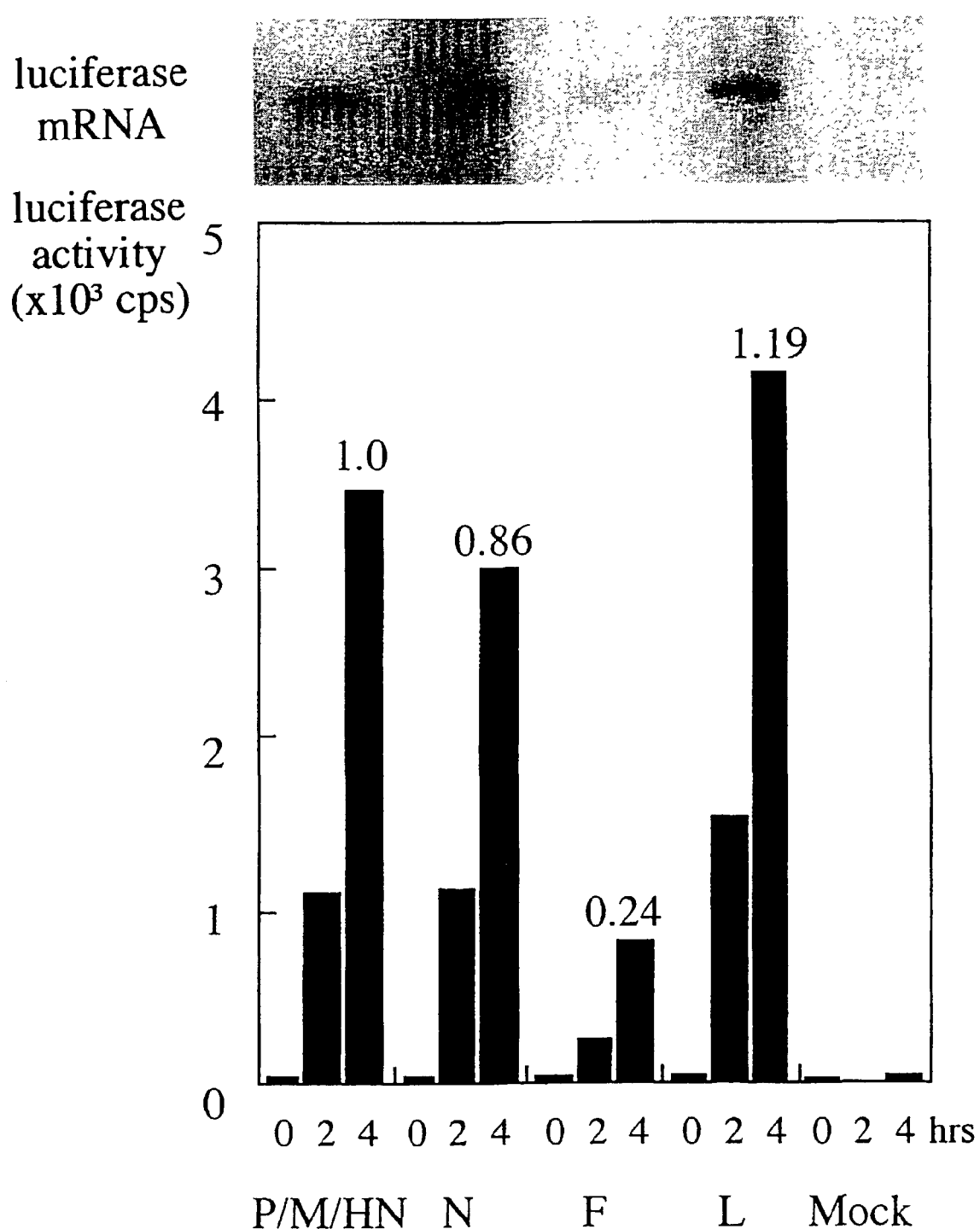
FIG. 4 is a photograph and graph showing luciferase expression of recombinant SeV. The recombinant viruses were inoculated to CV1 cells at an moi of 100 (pfu/cell). The cells were cultured in the presence of cycloheximide for 12 hr. Portions of cells were harvested to prepare RNA and probed with the luciferase probe (top). The remaining of cells was additionally incubated for 0, 2 and 4 hrs without cycloheximide to allow the protein synthesis and luciferase activity was measured (bottom).

In a similar manner as in Example 1, CV1 cells were infected with the recombinant viruses at an m.o.i. of 100, and the infected cells were incubated in the presence of 100 µg/ml cycloheximide (Sigma, St. Louis) for 12 h. The RNA in infected cells was prepared as described above, and the Northern hybridization was performed using the luciferase cDNA as the probe (FIG. 4, top). A different batch of cells was incubated to synthesize proteins in the absence of cycloheximide for 0, 2 and 4 h, and the luciferase activity was measured.

As a result, in all cells infected with any recombinant virus, it was found that the longer the incubation period was after cycloheximide removal, the higher the luciferase activity was. However, the luciferase expression of SeV/SfLuc-infected cells was again significantly lower than the other three (FIG. 4, bottom). The amounts of luciferase mRNA in each of the virus-infected cells correlated well with the activities of luciferase. The luciferase activities at 4 hr incubation were normalized by the count of SeV/SpLuc, as this type of S sequence is shared with three of the six genes. Luciferase activities in SeV/SnLuc- and SeV/SlLuc-infected cells were 0.86 and 1.19, respectively, and thus nearly comparable to that in SeV/SpLuc. In contrast, the value of SeV/SfLuc-infected cells reached only 0.24 of the control.

These results strongly suggested that the signal used for F gene expression possesses a lower reinitiation potential than the other S sequences.

EXAMPLE 3

SeV Mutant Comprising a Modified S Sequence for the F Gene

The results described above suggested that there is a down-regulation of transcription at the F gene in the natural genome context of SeV. To investigate this, the inventors next created mutant SeV, SeV/mSf, whose S sequence of the F gene was replaced with that of the P/M/HN gene, as described below and compared its replication with that of the wild-type.

3-1. Mutagenesis to Modify the S Sequence of F Gene in Full-Length SeV cDNA

Two nucleotides substitutions were performed on the S sequence of F gene as follows. First, pSeV(+) was cleaved by BanIII at the SeV potions of 2088 and 5333 in SeV genome, and the resulting 3.4 Kb-fragment was recloned into the same restriction site of pBluescript KS(+) (Stratagene, La Jolla) to make a pB/BanIII. Then, site-directed mutagenesis by a PCR-mediated overlap primer extension method (Ho, S. N. et al., 1989, Gene 77:51–59) was performed as described above using synthesized two primers (mGS1F; 5'-$^{4810}$CTTAGGG TGAAAGTCCCTTGT$^{4830}$-3'/SEQ ID NO: 13 and mGS1R; 5'-$^{4830}$ACAAGGGACTTTCACCCTAAG$^{4810}$-3'/SEQ ID NO: 14) and two outer primers (M1F, 5'-$^{3931}$TACCCATAG-GTGTGGCCAAAT$^{3951}$-3'/SEQ ID NO: 15 and T7 5'-TAATACGACTCACTATAGGGC-3'/SEQ ID NO: 16). Underlined letters are the mutagenized points. The first PCRs performed with M1F/mGS1R primer pairs and T7/mGS1F primer pairs using the pB/BanIII as a template yielded 0.9 Kb- and 0.6 Kb-fragment, respectively. These two fragments were purified, and the second PCR was then performed with M1F/T7 primer pairs using the purified fragments as the templates, generating a single 1.5 Kb-fragment with the two nucleotides mutations. This fragment was purified and digested with BanIII and recloned into the same restriction site of pSeV(+) to make a pSeV(+)mSf. The cloned sequence was verified by nucleotide sequencing. Viruses were reconstituted from the cDNA by the same procedures as Example 1.

Figure 5:
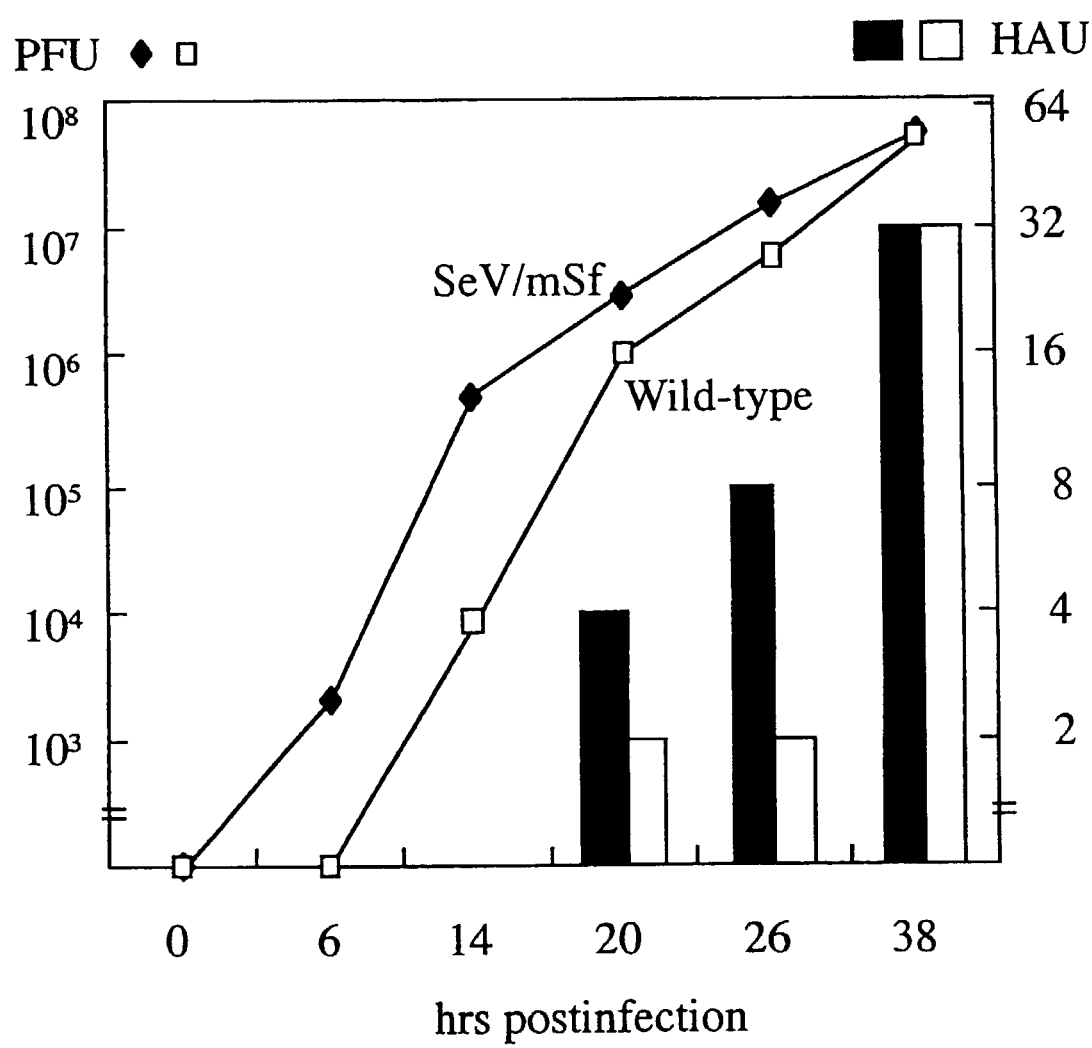
FIG. 5 shows growth kinetics of SeV/mSf. The titers of the wild-type SeV and mutant SeV/mSf were measured at the time points indicated under single-cycle conditions. Open bars and filled bars represent hemagglutination units (HAU) of wild-type and mutant viruses, respectively. Lines with open and filled circles represent pfu per ml of the wild-type and mutant viruses, respectively.
Figure 6:
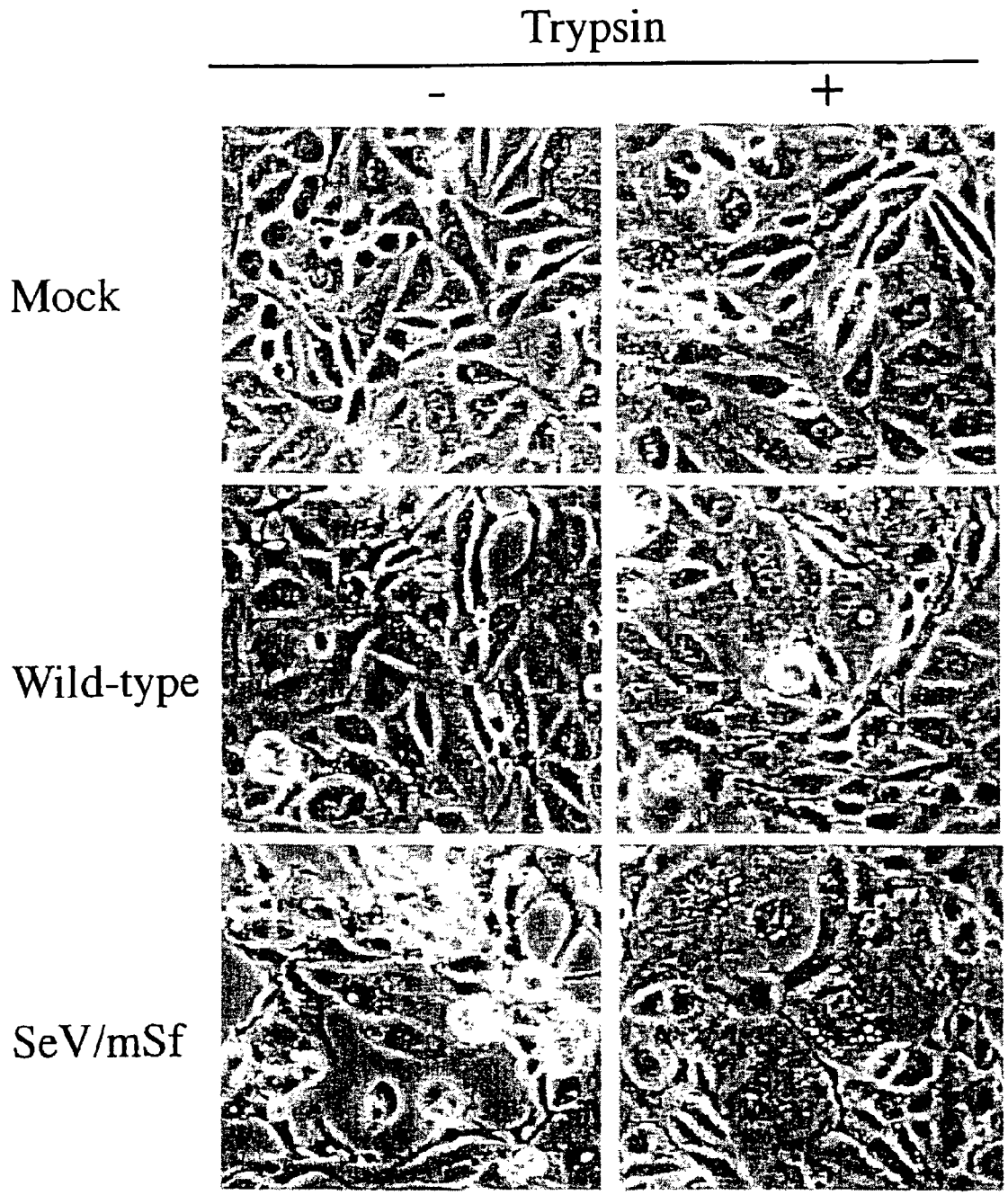
FIG. 6 is a photograph showing cytopathogenecity of SeV/mSf. CV1 cells were infected with the wild-type or SeV/mSf virus at an moi of 20 (pfu/cell) in the presence (+) and absence (−) of trypsin. The pictures were taken 48 hr post infection

The proliferation of this virus was examined using CV1 cells. The SeV/mSf was found to grow faster than the wild-type SeV in CV1 cells (FIG. 5). In the absence of trypsin, round cells and detached cells were observed. In the presence of exogenous trypsin to proteolytically activate the F glycoprotein, fused cells were observed more for the SeV/mSf than for the wild-type (FIG. 6).

3-2. Expression of SeV/mSf Genes

The mRNA levels in CV1 cells infected with the wild-type and SeV/mSf at moi=10 were analyzed by Northern blotting like Example 1 at various hours p.i. For the Sendai virus N probe, the PstI/PvuI (1189 bp) fragment was purified from the pGEM-N and used. For P probe, 792 bp of SmaI/SmaI fragment was purified from the pGEM-P and used. For M, F, HN and L probes, the NdeI/NdeI (878 bp), BamHI/BamHI (902 bp), ScaI/ScaI (1108 bp) and BamHI/BamHI (1654 bp) fragments were purified from pSeV(+) and used, respectively.

Figure 7:
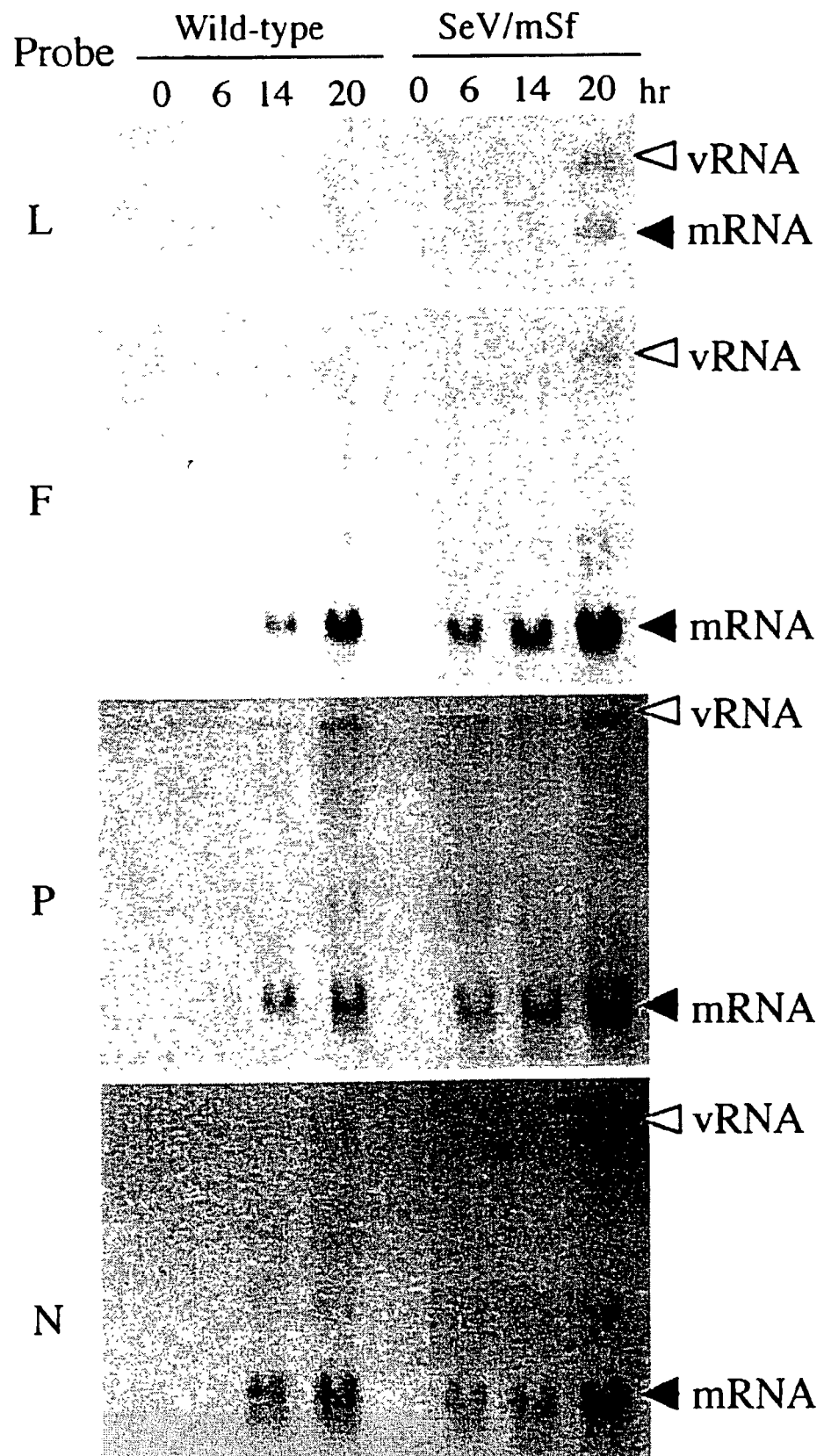
FIG. 7 is a photograph showing intracellular expression of viral genes. CV1 cells infected with the wild-type SeV or SeV/mSf virus were analyzed by Northern hybridization with the viral N, P, F or L gene probes at various times (hrs) post infection. The positions of mRNAs and genomic/antigenomic RNA (vRNA) are marked.

As shown in FIG. 7, the F and L transcripts from SeV/mSf were detected earlier and reached remarkably higher levels, compared with the wild-type infection. The P and N transcripts were also detected earlier in SeV/mSf infection, although the peak levels were comparable to the wild-type.

Figure 8:
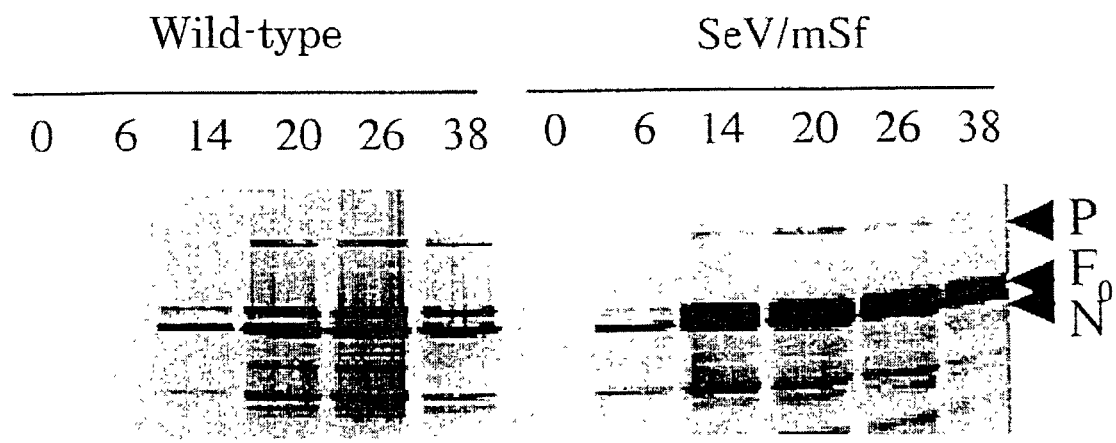
FIG. 8 is a photograph showing intracellular expression of viral genes. Intracellular expression of viral genes in CV1 cells was analyzed on Western blotting with anti-SeV antibody at various times (hrs) indicated at the top of each lane.

In order to confirm viral protein expression in infected cells, Western blotting was performed by using anti-SeV antibody. CV1 cells ($2\times10^5$) grown in 6-well plates were infected at a moi of 10 with the wild-type or SeV/mSf and harvested various hrs post infection. The cells were centrifuged, and the cell pellets were lysed and run in 12.5% SDS-PAGE (Laemmli, U. K., 1970, Nature 227:680–685) and analyzed by Western blotting with anti SeV rabbit serum as described (Kato, A. et al., 1995, Virology 209:480–488; Kato, A. et al., 1996, Genes to Cells 1: 569–579). As a result, the levels of $F_0$ protein in the SeV/mSf-infected cells were significantly higher than in the wild-type (FIG. 8) at any time point throughout infection. The downstream gene products, HN and L, were not well resolved in this experiment.

Figure 9:
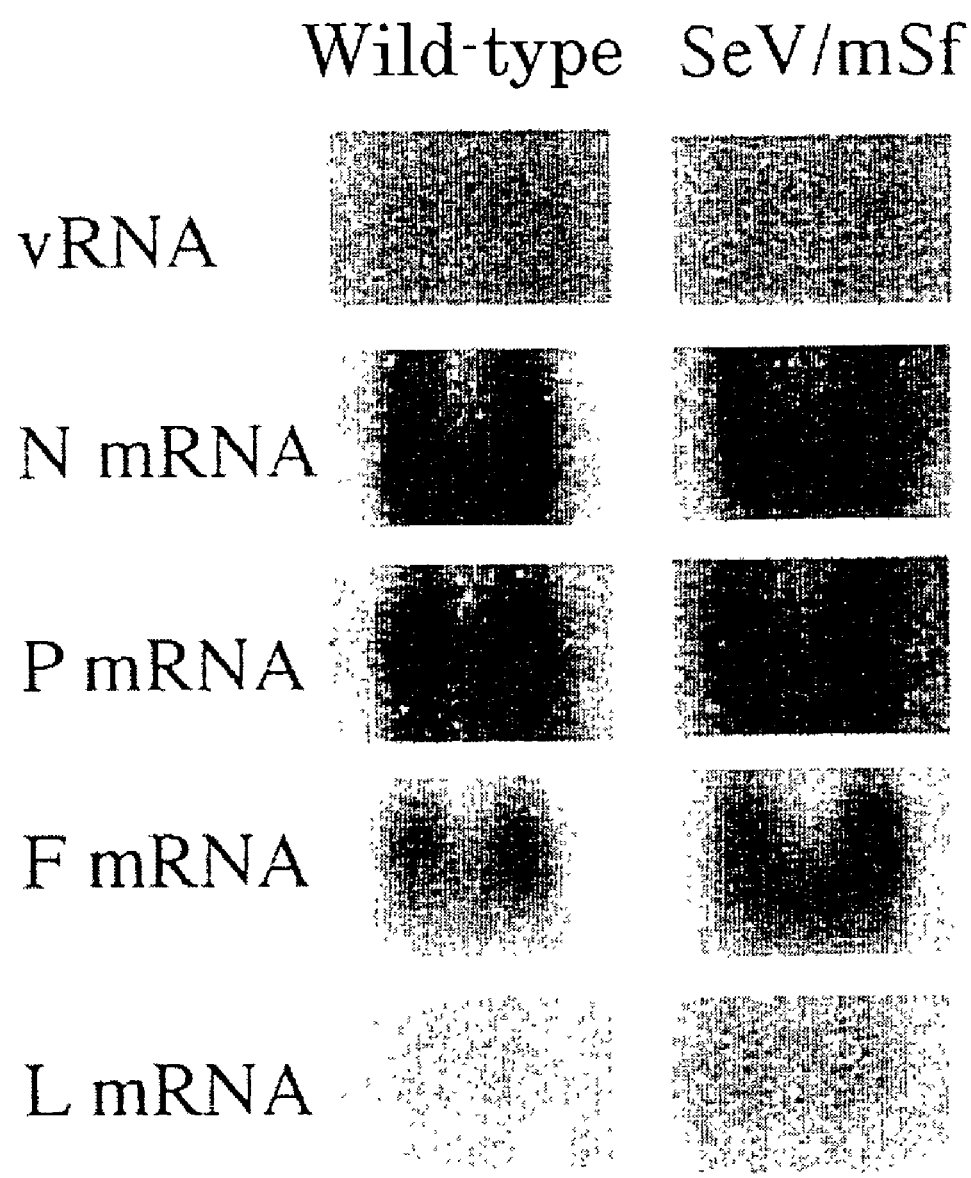
FIG. 9 is a photograph showing intracellular expression of viral genes. CV1 cells were infected with wild-type SeV and SeV/mSf at moi of 100 pfu in the presence of cycloheximide. RNAs were extracted after 12 hr inoculation and analyzed by Northern hybridization. The specific bands obtained were analyzed using the BAS 2000 Image Analyzer.

To compare the level of transcription directly, after the cells infected with either wild-type SeV or SeV/mSf were treated with cycloheximide to block de novo protein synthesis, RNAs were extracted from the cells and analyzed by Northern hybridization as above. The radioactivities of viral genomic RNA contained in hybridized bands were analyzed by using the BAS 2000 Image Analyzer (Fujifilm, Tokyo) Enhanced expression of the F and L genes, but not of the N and P gene, was also clearly seen in mutant SeV (FIG. 9). These results again unequivocally demonstrated that the S sequence naturally occurring for the F gene transcription possesses a lower reinitiation activity and hence down-regulates the expression of F and downstream genes. Therefore, it was also shown that transcription level of not only F gene but also downstream genes thereof can be elevated by replacing the S sequence of the F gene with one having high efficiency. Probably because of enhanced L gene expression in the SeV/mSf, the virion (v) RNA levels were higher for the mutant than for the wild-type throughout infection (FIG. 7). Earlier detection of mRNAs in the mutant SeV infected cells as demonstrated in FIG. 7 might be also due to the increased L gene expression.

EXAMPLE 4

Successive Co-Passages of the Wild-Type SeV and SeV/mSf in Embryonated Hen Eggs Although the wild-type SeV replicated slower than SeV/mSf in CV1 cells under single-cycle conditions as shown in FIG. 5, the possibility still remained that, when cultured slowly at multiple-cycle conditions, the naturally occurring down-regulation of transcription for the F and downstream genes would be more advantageous than the artificially introduced up-regulation. The inventors thus examined whether either the wild-type SeV or SeV/mSf would compete out the other under the multiple-cycle conditions of successive co-passages of the two viruses in eggs.

Figure 10:
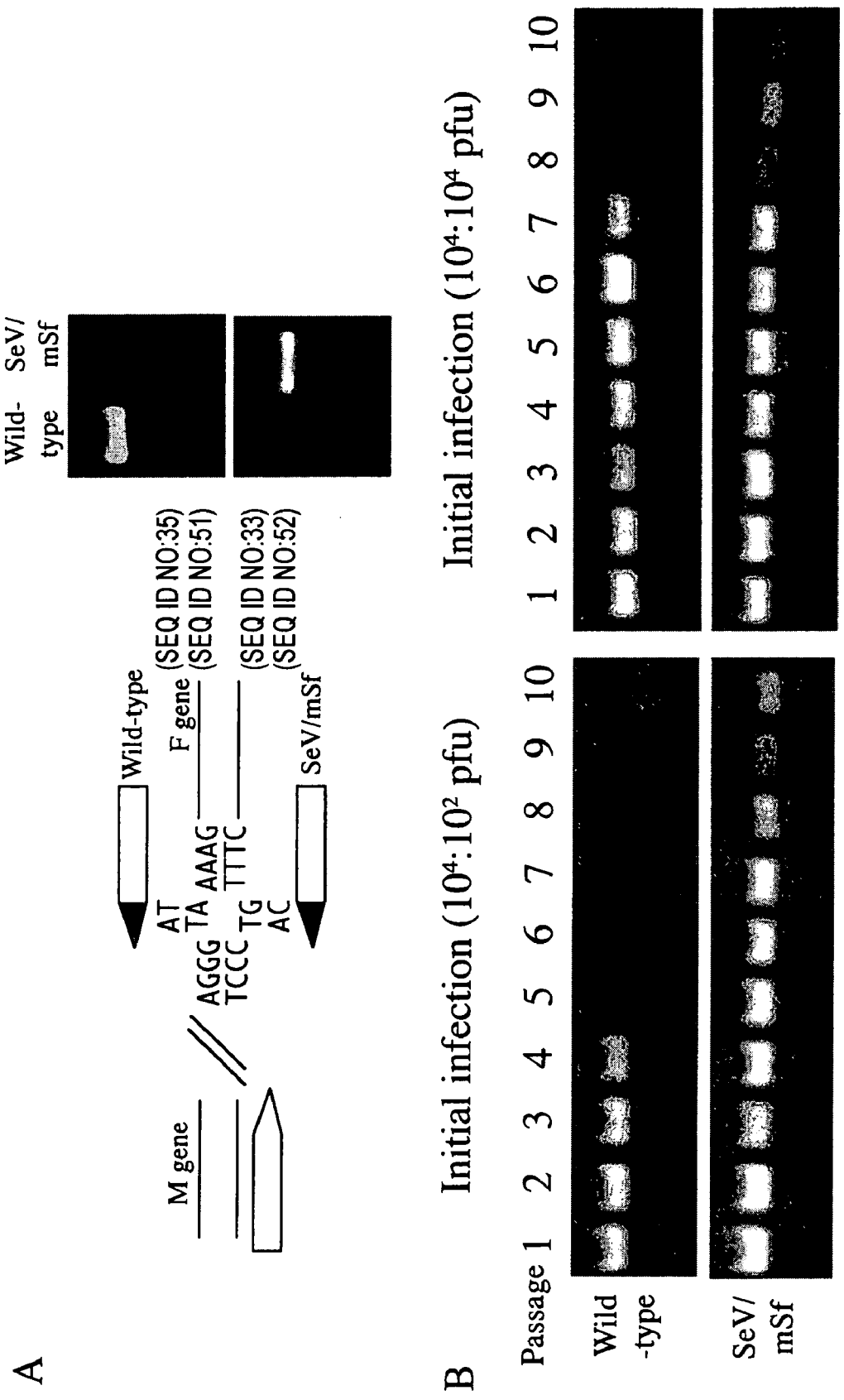
FIG. 10 is a photograph showing competition assays of the wild-type SeV and SeV/mSf in serial copassages. (A) The specific primer sets (left) to detect either of viral RNAs (right). (B) Each passage was initiated with input doses of $10^4$ (SeV/mSf) and $10^4$ (wild-type SeV) pfu/egg or $10^4$ (SeV/mSf) and $10^2$ (wild-type SeV) pfu/egg. The allantoic fluids were harvested every 3 days, diluted to $10^{-6}$ and co-inoculated into new eggs serially up to 10 passages. Viral RNAs were extracted and analyzed by one-step RT-PCR method using the specific primer sets. Passage number is shown on the top of each lane. "Wild-type" and "SeV/mSf" represent DNA fragments amplified by using specific primer sets for respective sequences.

The SeV/mSf and wild-type SeV were co-inoculated into two embryonated hen eggs with the respective doses of both $10^4$ pfu/egg ($10^4$:$10^4$ inoculation), and in another experiment, $10^4$ and $10^2$ pfu/egg($10^4$:$10^2$ inoculation). Every three days post inoculation, the allantoic fluids were harvested and after dilution to $10^{-6}$, 0.1 ml of this was reinoculated into new eggs. These reinoculations were successively repeated 10 times. Viral RNAs were extracted from each allantoic fluid by using TRIzol/LS (Gibco BRL, N.Y.) as Example 1, and amplified by one-step RT-PCR with two sets of specific primers. The viruses grown in the allantoic fluids were semi-quantitatively measured by RT-PCR with specific primer pairs. One primer pair was designed to amplify only fragments having wild-type S sequence for the F gene (AGGGatAAAG), (SEQ ID NO: 35), and the other mutant sequence (AGGGtgAAAG) (SEQ ID NO: 33) (FIG. 10A). Specifically, the RNA was extracted from 25 μl of each allantoic fluid, and reverse transcribed with HvM primer (5'-$^{4448}$TTTTCTCACTTGGGTTAATC$^{4467}$-3'/SEQ ID NO: 17) at 50° C. for 30 min using Superscript II (Gibco BRL, N.Y.), and were heat denatured at 94° C. for 2 min. The cDNAs were amplified by PCR with HvM and GS2WR (5'-$^{4836}$GCACTCACAAGGGACTTTca$^{4817}$-3'/SEQ ID NO: 18) primers for SeV/mSf and with HvM and GS2MR (5'-$^{4836}$GCACTCACAAGGGACTTTat$^{4817}$-3'/SEQ ID NO: 19) primers for wild-type SeV as described previous (Kato, A. et al., 1997, EMBO J. 16:578–587; Kuronati, A. et al., 1998, Genes Cells 3:111–124). The lower case letters represent the mutated dinucleotides. The respective specific products were analyzed by electrophoresis in agarose gel as described.

It was found that the wild-type genome had disappeared by the eighth passage in the case of $10^4$:$10^4$ inoculation and by fifth passages following $10^4$:$10^2$ inoculation (FIG. 10B). In control experiments, each virus was individually passaged and the genome sequences were determined. The results indicated that both of the viral genomes were stably maintained during 10 successive passages without any nucleotide change in the regions sequenced. These data indicated that the naturally occurring F gene S sequence conferred no replication advantage on SeV at least in ovo under the multiple-cycle conditions.

EXAMPLE 5

Virulence of SeV/mSf in Mice

Highly complicated conditions are required for exhibiting virulence of SeV in natural host mice at individual level, compared with cultured cells or eggs. Whether the mutant SeV/mSf replicates earlier than the wild-type and shows stronger virulence in mice was examined.

Figure 11:
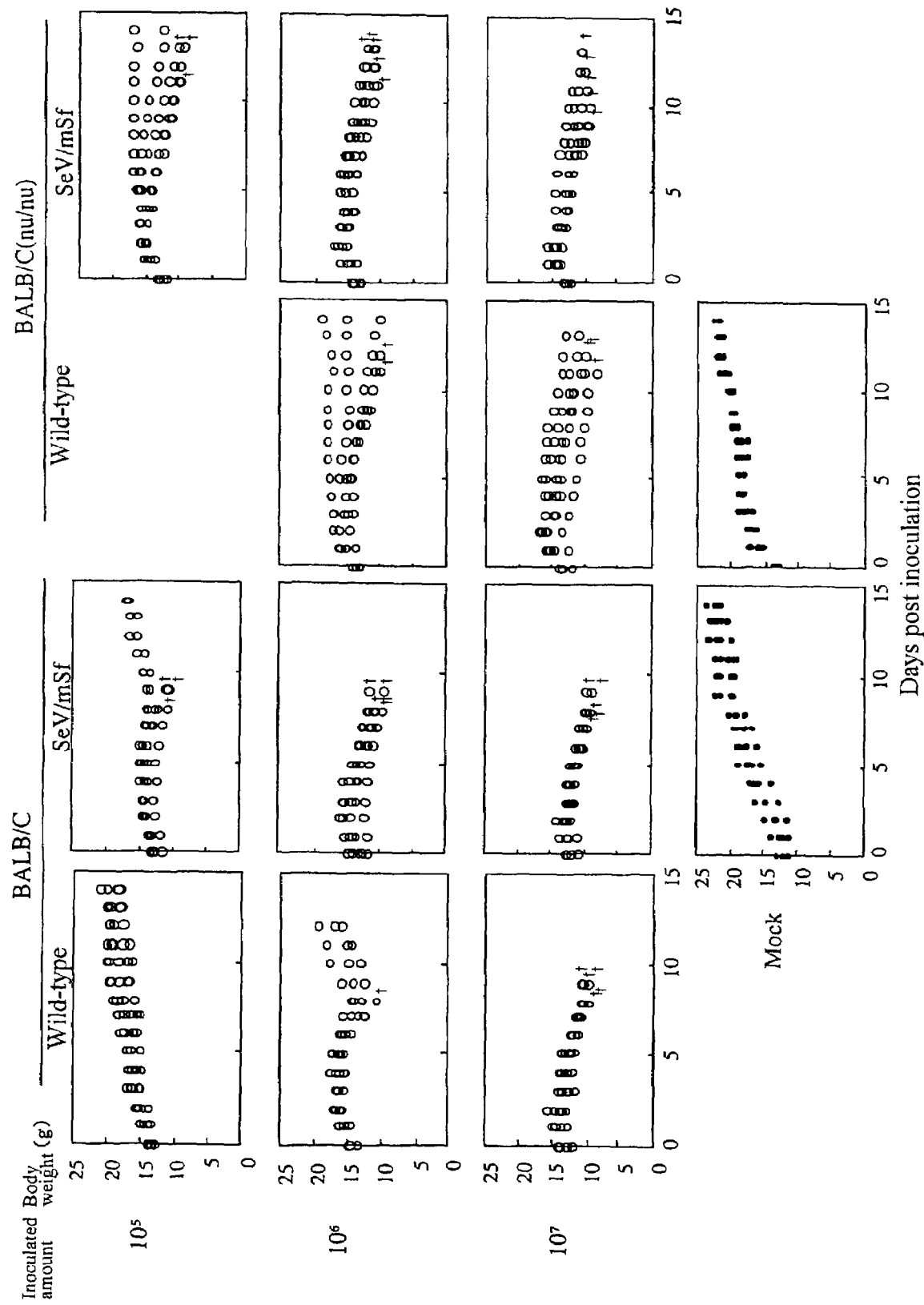
FIG. 11 shows body weight gain of normal BALB/c and thymus deficient BALB/c (nu/nu) mice infected with the wild-type SeV and SeV/mSf viruses. Five mice were inoculated intranasally with various doses of viruses ($10^4$ to $10^7$ pfu per mouse). The weight gain of mice were measured in grams every day up to 14 days post inoculation. Dead mice are marked by †.

Specific pathogen-free (SPF), 3-week-old of mice BALB/c and 4-week old of nude mice BALB/c (nu/nu) were purchased from Charles-River, Japan and used for virus infection experiments. These mice were infected intranasaly with $10^4$, $10^5$, $10^6$, $10^7$ or $10^8$ pfu/mouse of the wild-type or SeV/mSf under mild anesthetization with ether (Kiyotani, K. et al., 1990, Virology 177:65–74). Their body weights were individually measured every day up to 14 days. At 0, 1, 3, 5, 7 and 9 days post infection, three mice in each group were sacrificed and the virus titers in the lungs were measured for BALB/c and nude mice inoculated with $10^4$ pfu. Pulmonary lesions were scored at the same time (Kato, A. et al., 1997, EMBO J. 16:578–587). The results are shown in FIG. 11.

The mouse body weight gain was strongly disturbed by $10^7$ pfu of both virus inoculations. All mice were killed by either virus at similar days p.i. At $10^6$ pfu significant differences were found between the two viruses. SeV/mSf more strongly affected the body weight gain compared with the wild-type. The former killed all mice while the latter killed only one and allowed the remaining mice to gain the weight again. At $10^5$ pfu, all mice infected with the wild-type showed a pattern of weight gain nearly comparable to that of the mock infected mice, and survived, while those infected with the mutant SeV/mSf did not and half of the mice died. Thus, SeV/mSf was clearly more virulent than the wild-type. The difference in virulence was quantitated by 50% lethal dose ($LD_{50}$); the $LD_{50}$ was $1.78 \times 10^6$ pfu for the wild-type and $7.94 \times 10^4$ pfu for the mutant (Table 1). The mutant virus was thus 22 times more virulent than the wild-type for BALB/c strain.

TABLE 1

$LD_{50}$ of wild-type and mutant viruses in normal and nude mice

| Inoculation | | BALB/C | $LD_{50}$ | BALB/C(nu/nu) | $LD_{50}$ |
|---|---|---|---|---|---|
| Wild-type | $10^8$ | 5/5[a] | $1.78 \times 10^6$ | NT | $3.16 \times 10^6$ |
| | $10^7$ | 5/5 | | 3/5 | |
| | $10^6$ | 1/4 | | 2/5 | |
| | $10^5$ | 0/5 | | NT | |
| | $10^4$ | 0/5 | | 0/5 | |
| SeV mS/F | $10^8$ | 5/5 | $7.94 \times 10^4$ | NT | $7.94 \times 10^4$ |
| | $10^7$ | 5/5 | | 5/5 | |
| | $10^6$ | 5/5 | | 5/5 | |
| | $10^5$ | 3/5 | | 3/5 | |
| | $10^4$ | 0/5 | | 0/5 | |

[a]Dead individuals/Inoculated individuals

Figure 12:
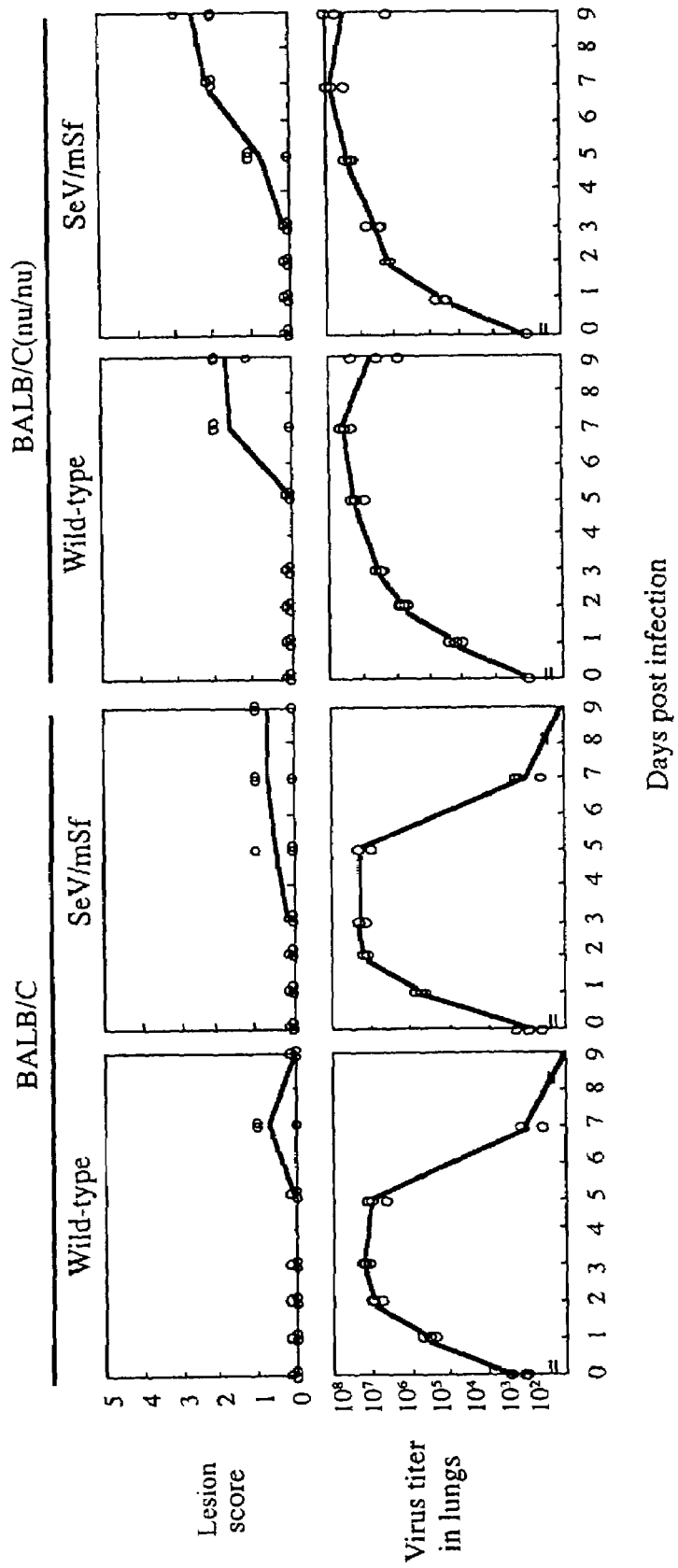
FIG. 12 shows pulmonary lesions and viral loads in the lungs of BALB/c and BALB/c (nu/nu) mice. Each mouse was intranasally inoculated with $10^4$ pfu of the viruses. These mice were sacrificed at 0, 1, 2, 3, 5, 7 and 9 days post inoculation to grade lesion scores (top) and to determine virus titers in the lungs (bottom). All these values are individually shown for each mouse.

Cytotoxic T lymphocytes (CTL) modulate SeV pathogenesis in two different ways. They contribute to eliminating or clearing the virus from body on one hand, and on the other, accelerate disease progression by immunopathological processes. That is, experimental results in BALB/c mice indicate the possibility of indirect exacerbation due to an enhanced immuno response induced by the mutant SeV, rather than direct effects resulting from a high reproducibility of the mutant SeV in the mouse body. Therefore, in an attempt to deny the possibility of aggravated pathogenicity resulting from an induced immunity, pathogenicities of the wild type and mutant viruses were compared in thymus-deficient nude mice (FIG. 11). The $LD_{50}$ values of each virus were comparable for nude mice and for the parental normal mice, and a similar difference (to 40 fold) between the two viruses was found for the nude mice (Table 1). These results suggested that CTL did not play a major role in pathogenesis of both wild-type and mutant viruses during the observation period (14 days) at least on the bases of $LD_{50}$. However, both the wild-type and mutant viruses persisted in the lungs of nude mice throughout, while cleared in the parental mice (FIG. 12). These results suggest that CTL and other thymus-dependent responses play at least partial roles in the virus pathology.

From the above-described results, it has been indicated that the natural S sequence of the F gene partially suppresses the replication of SeV so as to allow infected mice to survive for a longer time.

EXAMPLE 6

Construction of S Sequence-Converted, F-Deficient Genomic cDNA

Figure 13:
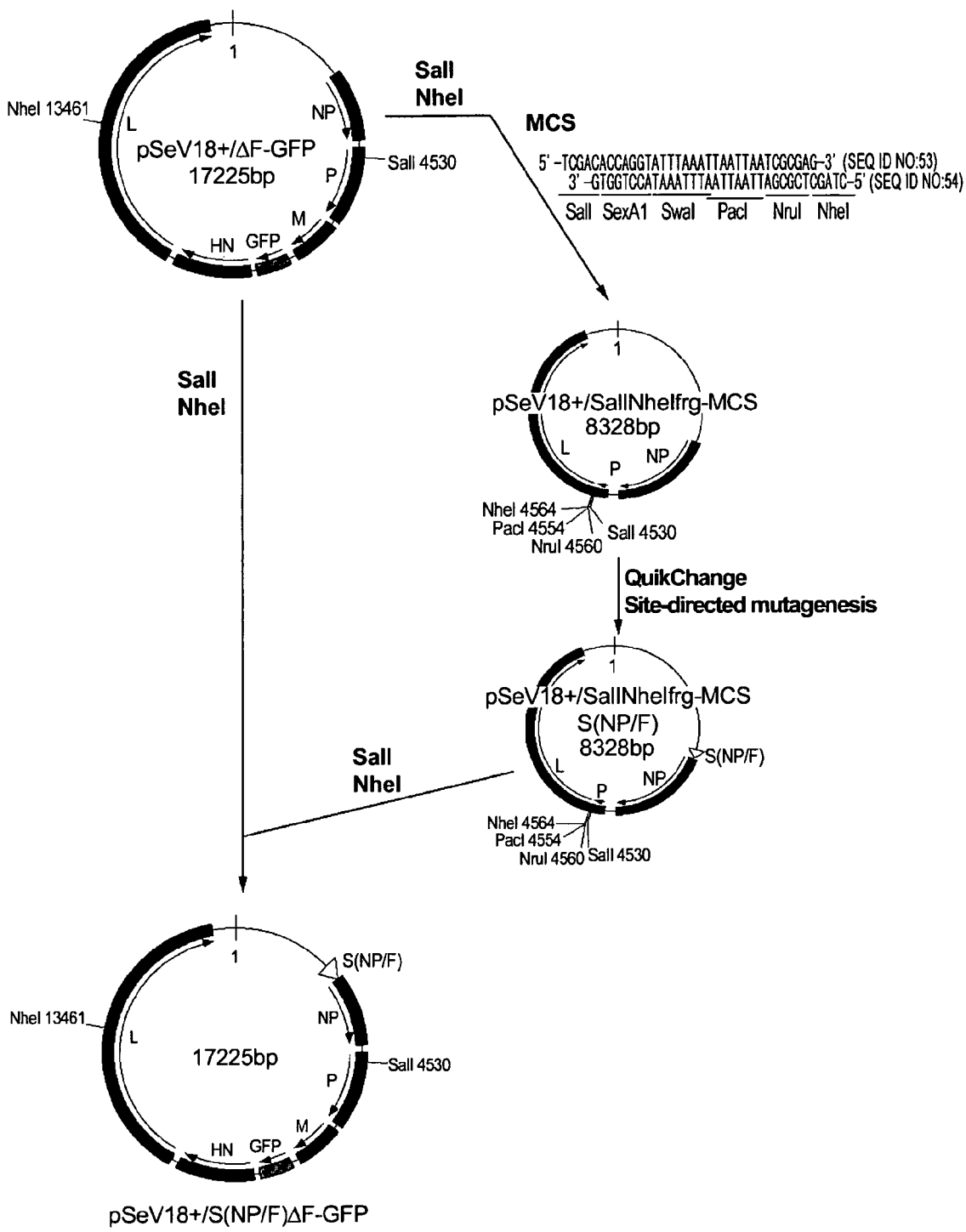
FIG. 13 shows a construction scheme of the plasmid encoding genomic cDNA of F-deficient SeV in which the S sequence of N gene has been converted into that of F gene.

FIG. 13 shows a construction scheme for the genomic cDNA of F-deficient SeV (pSeV18+/S(N/F)ΔF-GFP) in which the S sequence of N gene had been converted to the S sequence of F gene. A full-length genomic cDNA of F-deficient SeV carrying the EGFP gene at the F-deleted site (pSeV18+/ΔF-GFP: Li, H.-O. et al., J. Virology 74, 6564–6569 (2000), WO00/70070) was digested with SalI and NheI, and the fragment (8294 bp) containing the N gene was separated by agarose gel electrophoresis. The band corresponding to the fragment was excised, recovered using the QIAEXII Gel Extraction System (QIAGEN, Bothell, Wash.), and a multicloning site was inserted utilizing synthetic oligo DNAs (construction of pSeV/ΔSalINheIfrg-MCS). Sequences of synthetic oligo DNAs used for the insertion of the multicloning site are (5'-tcgacaccaggtatt-taaattaattaatcgcgag-3'/SEQ ID NO: 20; 5'-ctagctcgcgattaat-taatttaaatacctggtg-3'/SEQ ID NO: 21). Mutagenesis was performed on this pSeV/ΔSalINheIfrg-MCS using the QuikChange™ Site-Directed Mutagenesis Kit (Stratagene, La Jolla, Calif.) according to the instruction described in the Kit. Sequences of synthetic oligo DNAs used for mutagenesis are (5'-gaagttatacaggattttagggataaagtatccaccctgaggag-3'/SEQ ID NO: 22; 5'-ctcctcagggtggatactttatc-cctaaaatcctgtataacttc-3'/SEQ ID NO: 23). pSeV/ΔSalINheIfrg-MCS in which the S sequence of N gene had been converted into the S sequence of F gene (pSeV/ΔSalINheIfrg-MCS S (N/F)) was digested with SalI/NheI to recover a fragment (8294 bp), while pSeV18+/ΔF-GFP was digested with SalI/NheI to recover a fragment (8931 bp) containing M and HN genes, and such, and these two fragments were ligated to construct pSeV18+/S(N/F)ΔF-GFP.

Figure 14:
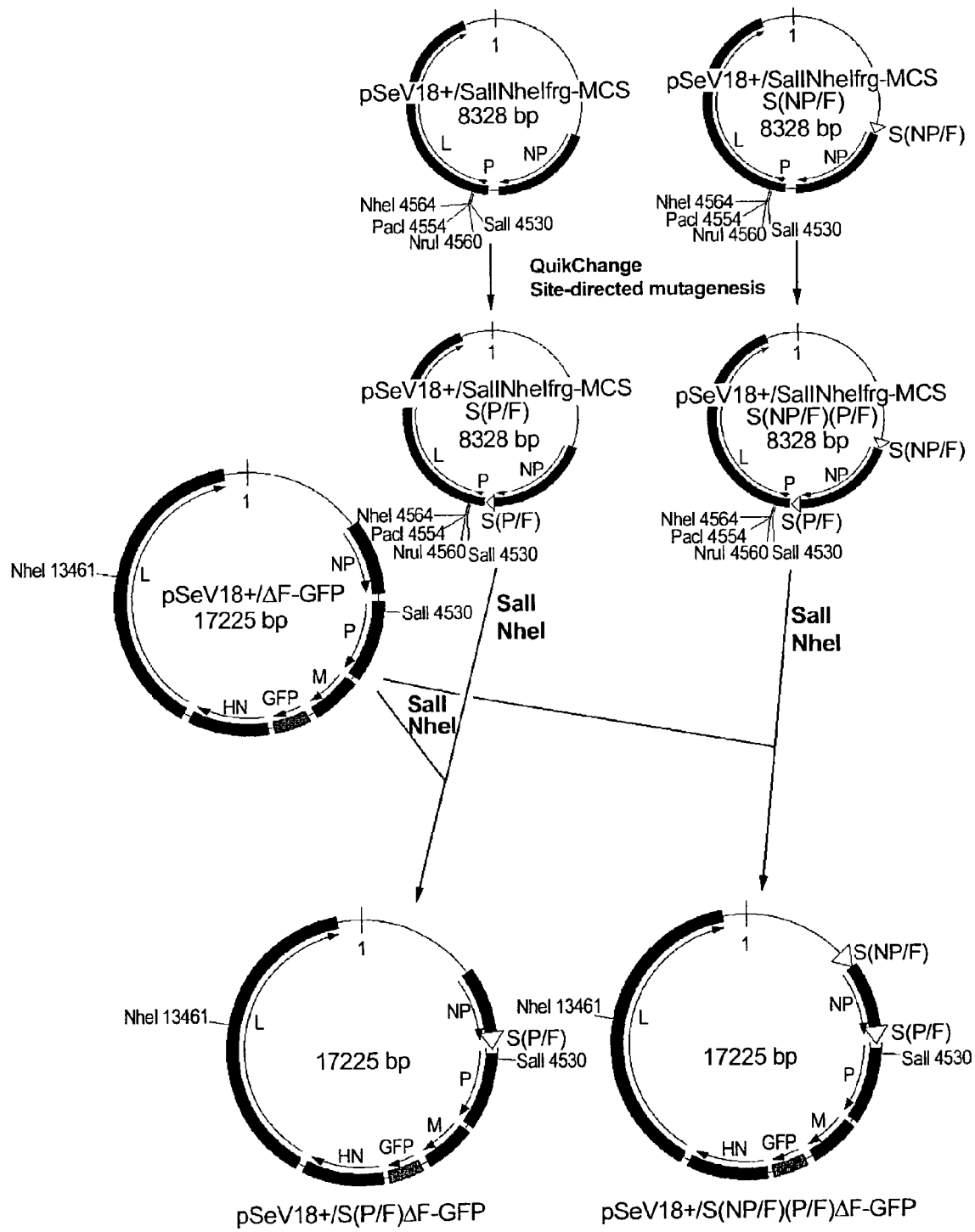
FIG. 14 shows construction schemes of the plasmids encoding genomic cDNAs of F deficient SeVs in which the S sequence of P gene has been converted into that of F gene, and in which the S sequences of N and P genes have been converted into that of F gene.

The genomic cDNA of F-deficient SeV in which the S sequence of P gene had been converted into the S sequence of F gene (pSeV18+/S(P/F)ΔF-GFP) and the genomic cDNA of F-deficient SeV in which the S sequences for both N and P genes had been converted into S sequence of F gene (pSeV18+/S(P/F)(N/F)ΔF-GFP) were constructed according to the above-described method as follows (FIG. 14). Mutagenesis was performed on pSeV/ΔSalINheIfrg-MCS and pSeV/ΔSalINheIfrg-MCS S(N/F)) respectively, using the QuikChange™ Site-Directed Mutagenesis Kit (Stratagene, La Jolla, Calif.) according to the instructions described in the Kit. Sequences of synthetic oligo DNAs used for mutagenesis are (5'-tccgtagtaagaaaaacttagg-gataaagttcatccaccgatcgg-3'/SEQ ID NO: 24; 5'-ccgatcggtg-gatgaactttatccctaagtttttcttactacgga-3'/SEQ ID NO: 25). After the mutagenesis, each plasmid was digested with SalI/NheI to recover fragments (8294 bp). These fragments were ligated respectively to a fragment (8931 bp) containing M and HN genes, and such, which had been recovered after digesting pSeV18+/ΔF-GFP with SalI/NheI, to construct pSeV18+/S(P/F)ΔF-GFP and pSeV18+/S(P/F)(N/F)ΔF-GFP.

EXAMPLE 7

Reconstitution and Amplification of Transcription S Sequence-Converted F-Deficient SeV Viral reconstitution was carried out according to the report of Li et al. (Li, H.-O. et al., J. Virology 74. 6564–6569 (2000), WO00/70070). In this case, since the virus is defective in F gene, helper cells to supply F protein are used, and the helper cells are prepared using the Cre/loxP expression inducing system. The system utilizes the plasmidp-CALNdLw (Arai, T. et al., J. Virol. 72: 1115–1121 (1998)) designed so as to induce the expression of gene product with CreDNA recombinase, in which a transformant of the plasmid is infected with a Cre DNA recombinase-expressing recombinant adenovirus (AxCANCre) by the method of Saito, et al. (Saito, I. et al., Nucl. Acid. Res. 23, 3816–3821 (1995); Arai, T. et al., J. Virol. 72, 1115–1121 (1998)) to express inserted genes. In the case of SeV-F protein, the transformant cells containing the F gene are referred to as LLC-MK2/F7, and cells continuously expressing F protein after the induction with AxCANCre are referred to as LLC-MK2/F7/A.

The virus having the modified S sequence was reconstituted as follows. LLC-MK2 cells were plated on 100-mm diameter Petri dishes at $5 \times 10^6$ cells/dish, cultured for 24 h, and then infected with a recombinant vaccinia virus expressing T7 polymerase, which had been treated with the long-wavelength ultraviolet light (365 nm) for 20 min in the presence of psoralen (PLWUV-VacT7: Fuerst, T. R. et al., Proc. Natl. Acad. Sci. USA 83, 8122–8126 (1986)) at room temperature for 1 h (m.o.i.=2). After the cells were washed with serum-free MEM, the plasmid constructed in Example 6 [pSeV18+/S(N/F)ΔF-GFP, pSeV18+/S(P/F)ΔF-GFP, or pSeV18+/S (P/F) (N/F)ΔF-GFP], pGEM/N, pGEM/P, pGEM/L, and pGEM/F-HN (WO00/70070) (Kato, A. et al., Genes Cells 1, 569–579 (1996)) were suspended in Opti-MEM (Gibco-BRL, Rockville, Md.) at weight ratios of 12 µg, 4 µg, 2 µg, 4 µg and 4 µg/dish, respectively. To the suspension, 1 µg DNA/5 µl equivalent SuperFect (Qiagen, Bothell, Wash.) were added and mixed. The mixture was allowed to stand at room temperature for 15 min and finally added to 3 ml of Opti-MEM containing 3% FBS. After the cells were washed with a serum-free MEM, the mixture was added to the cells and the cells were cultured. After cultured for 5 h, the cells were washed twice with a serum-free MEM, and then cultured in MEM containing 40 µg/ml of cytosine β-D-arabinofuranoside (AraC: Sigma, St. Louis, Mo.) and 7.5 µg/ml of trypsin (Gibco-BRL, Rockville, Md.). After cultured for 24 h, cells continuously expressing F protein (LLC-MK2/F7/A: Li, H.-O. et al. , J. Virology 74. 6564–6569 (2000), WO00/70070) were layered at $8.5 \times 10^6$ cells/dish, and cultured in MEM containing 40 µg/ml of AraC and 7.5 µg/ml of trypsin for further 2 days at 37° C. (P0). These cells were recovered, and the pellet was suspended in 2 ml/dish of Opti-MEM. After three repeated cycles of freezing and thawing, the lysate thus obtained was transfected as a whole to LLC-MK2/F7/A cells, and the cells were cultured using a serum-free MEM containing 40 µg/ml of AraC and 7.5 µg/ml of trypsin at 32° C. (P1). Five to seven days later, an aliquot of the culture supernatant was sampled and infected to freshly prepared LLC-MK2/F7/A cells, and the cells were cultured using the serum-free MEM containing 40 μg/ml of AraC and 7.5 μg/ml of trypsin at 32° C. (P2). Three to five days later, the supernatant was infected again to freshly prepared LLC-MK2/F7/A cells, and the cells were cultured using a serum-free MEM containing only 7.5 μg/ml of trypsin at 32° C. for 3 to 5 days (P3). To the culture supernatant thus recovered, BSA was added to make a final concentration of 1%, and the resulting mixture was stored at −80° C. The stored virus solution was thawed and used in subsequent experiments.

Titers of virus solutions prepared by this method were $1.2 \times 10^8$, $2.4 \times 10^8$, and $1.6 \times 10^8$ GFP-CIU/ml (the definition of GFP-CIU was described in WO00/70070) for SeV18+/S(N/F)ΔF-GFP, SeV18+/S(P/F)ΔF-GFP, and SeV18+/S(P/F)(N/F)ΔF-GFP, respectively.

EXAMPLE 8

Cytotoxicity of Transcription S Sequence-Converted F-Deficient SeV (LDH Assay)

Figure 15:
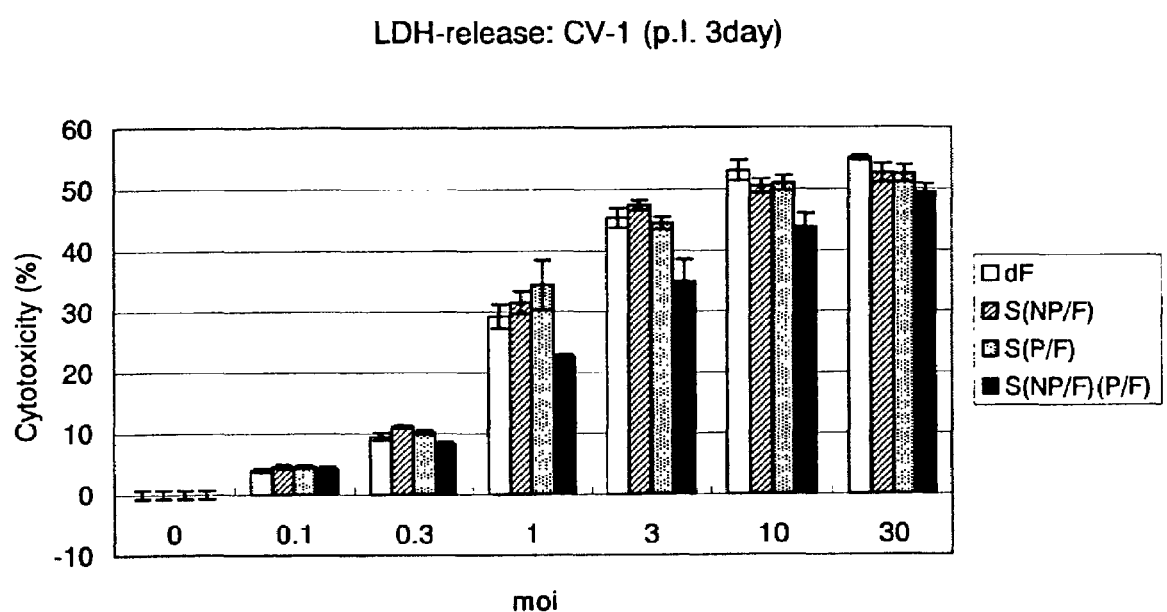
FIG. 15 shows the cytotoxicity measured by the release of LDH in the culture medium 3 days after CV-1 cells were infected with SeV18+/ΔF-GFP, SeV18+/S(N/F)ΔF-GFP, SeV18+/S(P/F)ΔF-GFP or SeV18+/S (P/F) (N/F)ΔF-GFP at m.o.i. (s) of 0.1, 0.3, 1, 3, 10 and 30, and cultured in a serum-free medium.

Cells are often injured by the SeV infection. Since cytotoxic effects can be clearly observed especially in CV-1 cells, cytotoxicity was assessed using these cells. By converting the S sequence of a gene to that of the F gene, it is expected that transcription and/or replication levels of genes downstream thereof will be reduced (transcription and/or replication is suppressed). Therefore, it was examined whether any changes in cytotoxicity would occur when the transcription and/or replication was suppressed. CV-1 cells were seeded into a 96-well plate ($2.5 \times 10^4$ cells/well, 100 μl/well) and cultured. MEM containing 10% FBS (Gibco-BRL, Rockville, Md.) was used as the culture medium. After a 24-hour culture, the cells were infected by adding 5 μl/well each of SeV18+/S(N/F)ΔF-GFP, SeV18+/S(P/F)ΔF-GFP or SeV18+/S(P/F)(N/F)ΔF-GFP solutions diluted with MEM containing 1% BSA, and 6 h later, the medium containing the virus solution was removed and replaced by a FBS-free medium. Three days after the infection, samples were withdrawn from culture supernatants, cytotoxicity levels were quantitated using the Cytotoxicity Detection Kit (Roche, Basel, Switzerland) according to the instructions described in the kit. F-deficient SeV with no mutation in the S sequence (SeV18+/ΔF-GFP: Li, H.-O. et al., J. Virology, 74, 6564–6569 (2000), WO00/70070) was used as a control. Although there was no difference in the cytotoxicity level in SeVs with a single conversion of the S sequence, such as SeV18+/S(N/F)ΔF-GFP and SeV18+/S(P/F)ΔF-GFP, a clear attenuation in cytotoxicity was observed by converting S sequences of both N and P genes to S sequence for the F gene (FIG. 15). That is, it was demonstrated that SeV infection-dependent cytotoxicity can be attenuated by suppressing transcription and/or replication through the conversion of S sequence.

EXAMPLE 9

Quantitation of Virion Formation from Cells Infected with Transcription S Sequence-Converted F-Deficient SeV As an index that reflects the transcription and/or replication rate, virion formation levels from infected cells were periodically measured. Since periodical quantitation was required, LLC-MK2 cells with relatively high resistance to SeV infection were used for evaluation. As a control, SeV18+/ΔF-GFP was used as described above. 100 μl/well each of $1 \times 10^7$ CIU/ml and $3 \times 10^7$ CIU/ml virus solutions (m.o.i. of 1 and 3) were added to LLC-MK2 cells grown till confluent on 6-well plates and infected for an hour. Then, the cells were washed with MEM, 1 ml of serum-free MEM per well was added with, and cultured at 37° C. Samples were taken every day, and fresh serum-free MEM (1 ml) was added to the wells immediately after the sampling, and culture and periodical samplings were continued.

Figure 16:
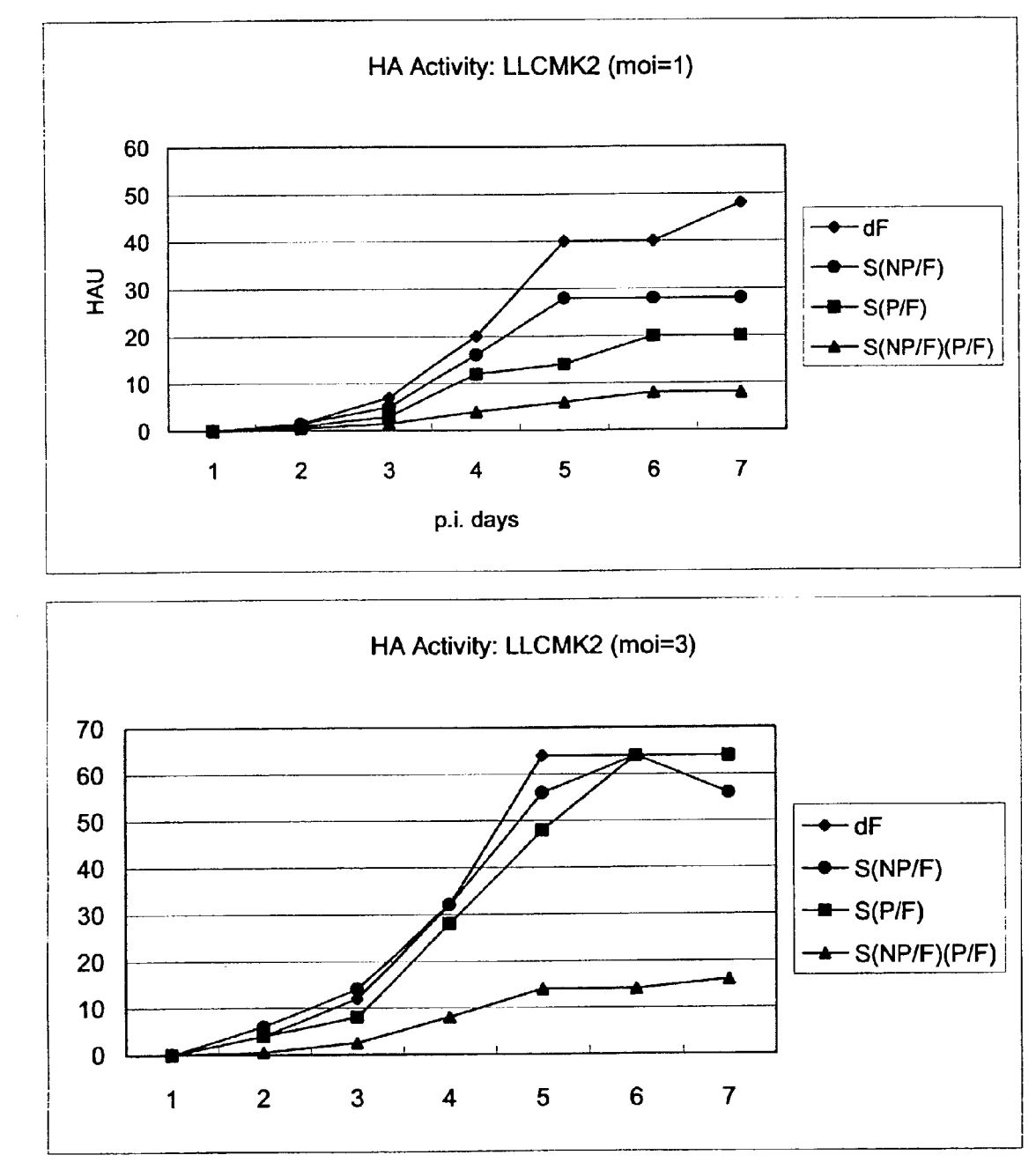

Virion formation from infected cells was quantitated by using the hemagglutination activity (HA activity) according to the method of Kato, et al. (Kato, A. et al., Genes Cells 1, 569–579 (1996)). That is, using round-bottomed 96-well plates, virus solutions were stepwise diluted with PBS to prepare a 2-fold serial dilution making the total volume in each well 50 μl. To that 50 μl was added 50 μl of a stock chicken blood diluted to 1% concentration in PBS (COSMO BIO, Tokyo, Japan), and the resulting mixture was allowed to stand at 4° C. for 1 h and examined for hemagglutination. Among agglutinates, the highest dilution rate at which hemagglutination occurred was described as the HA activity (FIG. 16). From the results of infection at an m.o.i. of 1, virion formation levels were slightly reduced with a single conversion of S sequence as in SeV18+/S(N/F)ΔF-GFP and SeV18+/S(P/F)ΔF-GFP, while further clearer decrease in virion formation levels was observed by converting S sequences of both N and P genes with that of the F gene as in SeV18+/S(P/F)(N/F)ΔF-GFP. At an m.o.i. of 3, although changes in virion formation levels with a single conversion of S sequence became almost negligible probably due to the increase in virus gene levels from the early stage of infection, a distinct decrease in the virion formation level was observed with SeV18+/S(P/F)(N/F)ΔF-GFP having S sequences of both N and P genes converted to that of the F gene under the experimental conditions. That is, the suppression of transcription and/or replication was confirmed by measuring virion formation. From this Example, it has been demonstrated that SeV infection-dependent cytotoxicity can be attenuated by introducing mutations into S sequences so as to suppress transcription and/or replication, such as in SeV18+/S(P/F)(N/F)ΔF-GFP.

INDUSTRIAL APPLICABILITY

The present invention provides virus vectors of Paramyxoviridae S sequences of which have been modified. In the virus vectors of this invention, S sequences have been modified so that transcription levels of genes on the genome have been modified compared to the wild type virus. These viruses are useful for elevating the virus proliferation capability and expression of a desired foreign gene. Such virus vectors are advantageous in improving the production efficiency of gene products. In contrast, in the case of proteins too high expressions of which are undesirable, it is possible to suppress expression levels of genes encoding the proteins by linking the genes to the downstream of the S sequence with the reduced reinitiation activity, such as the S sequence of F gene. Furthermore, by substituting the S sequences of N gene and/or P gene by the S sequence having a lower reinitiation activity, it is possible to suppress transcription and/or replication and reduce cytotoxicity of the vector genome. In addition, when recombinant virus particles or virus-like particles are recovered as pharmaceutical compositions or vaccines, viruses having a genome in which the S sequence has been modified to elevate the proliferation capability are advantageous in being capable of yielding a large amount of viruses in a short time.

SEQUENCE LISTING

```
<160> NUMBER OF SEQ ID NOS: 25

<210> SEQ ID NO 1
<211> LENGTH: 10
<212> TYPE: DNA
<213> ORGANISM: Artificial Sequence
<220> FEATURE:
<223> OTHER INFORMATION: artificially synthesized oligonucleotide
                        sequence

<400> SEQUENCE: 1
ctttcaccct                                                              10

<210> SEQ ID NO 2
<211> LENGTH: 15
<212> TYPE: DNA
<213> ORGANISM: Artificial Sequence
<220> FEATURE:
<223> OTHER INFORMATION: artificially synthesized oligonucleotide
                        sequence

<400> SEQUENCE: 2
tttttcttac tacgg                                                        15

<210> SEQ ID NO 3
<211> LENGTH: 18
<212> TYPE: DNA
<213> ORGANISM: Artificial Sequence
<220> FEATURE:
<223> OTHER INFORMATION: artificially synthesized oligonucleotide
                        sequence

<400> SEQUENCE: 3
gagggcccgc ggccgcga                                                     18

<210> SEQ ID NO 4
<211> LENGTH: 38
<212> TYPE: DNA
<213> ORGANISM: Artificial Sequence
<220> FEATURE:
<223> OTHER INFORMATION: artificially synthesized primer sequence

<400> SEQUENCE: 4
gagggcccgc ggccgcgata cgaggcttca aggtactt                               38

<210> SEQ ID NO 5
<211> LENGTH: 38
<212> TYPE: DNA
<213> ORGANISM: Artificial Sequence
<220> FEATURE:
<223> OTHER INFORMATION: artificially synthesized primer sequence

<400> SEQUENCE: 5
tcgcggccgc gggccctctg atcctagatt cctcctac                               38

<210> SEQ ID NO 6
<211> LENGTH: 48
<212> TYPE: DNA
<213> ORGANISM: Artificial Sequence
<220> FEATURE:
<223> OTHER INFORMATION: artificially synthesized primer sequence

<400> SEQUENCE: 6
caaagtatcc accccctga ggagcaggtt ccagacccctt tgctttgc                    48
```

```
<210> SEQ ID NO 7
<211> LENGTH: 19
<212> TYPE: DNA
<213> ORGANISM: Artificial Sequence
<220> FEATURE:
<223> OTHER INFORMATION: artificially synthesized primer sequence

<400> SEQUENCE: 7
ttaagttggt vagtgactc                                                  19

<210> SEQ ID NO 8
<211> LENGTH: 64
<212> TYPE: DNA
<213> ORGANISM: Artificial Sequence
<220> FEATURE:
<223> OTHER INFORMATION: artificially synthesized primer sequence

<400> SEQUENCE: 8
ttgcggccgc gtaagaaaaa cttagggtga aagttcactt cacgatggaa gacggcaaaa     60
acat                                                                  64

<210> SEQ ID NO 9
<211> LENGTH: 64
<212> TYPE: DNA
<213> ORGANISM: Artificial Sequence
<220> FEATURE:
<223> OTHER INFORMATION: artificially synthesized primer sequence

<400> SEQUENCE: 9
ttgcggccgc gtaagaaaaa cttagggtca aagttcactt cacgatggaa gacggcaaaa     60
acat                                                                  64

<210> SEQ ID NO 10
<211> LENGTH: 64
<212> TYPE: DNA
<213> ORGANISM: Artificial Sequence
<220> FEATURE:
<223> OTHER INFORMATION: artificially synthesized primer sequence

<400> SEQUENCE: 10
ttgcggccgc gtaagaaaaa cttagggata aagttcactt cacgatggaa gacggcaaaa     60
acat                                                                  64

<210> SEQ ID NO 11
<211> LENGTH: 64
<212> TYPE: DNA
<213> ORGANISM: Artificial Sequence
<220> FEATURE:
<223> OTHER INFORMATION: artificially synthesized primer sequence

<400> SEQUENCE: 11
ttgcggccgc gtaagaaaaa cttagggtga atgttcactt cacgatggaa gacggcaaaa     60
acat                                                                  64

<210> SEQ ID NO 12
<211> LENGTH: 31
<212> TYPE: DNA
<213> ORGANISM: Artificial Sequence
<220> FEATURE:
<223> OTHER INFORMATION: artificially synthesized primer sequence

<400> SEQUENCE: 12
tcgcggccgc tattacaatt tggactttcc g                                    31
```

<210> SEQ ID NO 13
<211> LENGTH: 21
<212> TYPE: DNA
<213> ORGANISM: Artificial Sequence
<220> FEATURE:
<223> OTHER INFORMATION: artificially synthesized primer sequence

<400> SEQUENCE: 13
cttagggtga aagtcccttg t                    21

<210> SEQ ID NO 14
<211> LENGTH: 21
<212> TYPE: DNA
<213> ORGANISM: Artificial Sequence
<220> FEATURE:
<223> OTHER INFORMATION: artificially synthesized primer sequence

<400> SEQUENCE: 14
acaagggact ttcaccctaa g                    21

<210> SEQ ID NO 15
<211> LENGTH: 21
<212> TYPE: DNA
<213> ORGANISM: Artificial Sequence
<220> FEATURE:
<223> OTHER INFORMATION: artificially synthesized primer sequence

<400> SEQUENCE: 15
tacccatagg tgtggccaaa t                    21

<210> SEQ ID NO 16
<211> LENGTH: 21
<212> TYPE: DNA
<213> ORGANISM: Artificial Sequence
<220> FEATURE:
<223> OTHER INFORMATION: artificially synthesized primer sequence

<400> SEQUENCE: 16
taatacgact cactataggg c                    21

<210> SEQ ID NO 17
<211> LENGTH: 20
<212> TYPE: DNA
<213> ORGANISM: Artificial Sequence
<220> FEATURE:
<223> OTHER INFORMATION: artificially synthesized primer sequence

<400> SEQUENCE: 17
ttttctcact tgggttaatc                      20

<210> SEQ ID NO 18
<211> LENGTH: 20
<212> TYPE: DNA
<213> ORGANISM: Artificial Sequence
<220> FEATURE:
<223> OTHER INFORMATION: artificially synthesized primer sequence

<400> SEQUENCE: 18
gcactcacaa gggactttca                      20

<210> SEQ ID NO 19
<211> LENGTH: 20
<212> TYPE: DNA
<213> ORGANISM: Artificial Sequence
<220> FEATURE:

-continued

<223> OTHER INFORMATION: artificially synthesized primer sequence

<400> SEQUENCE: 19
gcactcacaa gggactttat                                           20

<210> SEQ ID NO 20
<211> LENGTH: 34
<212> TYPE: DNA
<213> ORGANISM: Artificial Sequence
<220> FEATURE:
<223> OTHER INFORMATION: artificially synthesized primer sequence

<400> SEQUENCE: 20
tcgacaccag gtatttaaat taattaatcg cgag                            34

<210> SEQ ID NO 21
<211> LENGTH: 34
<212> TYPE: DNA
<213> ORGANISM: Artificial Sequence
<220> FEATURE:
<223> OTHER INFORMATION: artificially synthesized primer sequence

<400> SEQUENCE: 21
ctagctcgcg attaattaat ttaaatacct ggtg                            34

<210> SEQ ID NO 22
<211> LENGTH: 44
<212> TYPE: DNA
<213> ORGANISM: Artificial Sequence
<220> FEATURE:
<223> OTHER INFORMATION: artificially synthesized primer sequence

<400> SEQUENCE: 22
gaagttatac aggattttag ggataaagta tccaccctga ggag                 44

<210> SEQ ID NO 23
<211> LENGTH: 44
<212> TYPE: DNA
<213> ORGANISM: Artificial Sequence
<220> FEATURE:
<223> OTHER INFORMATION: artificially synthesized primer sequence

<400> SEQUENCE: 23
ctcctcaggg tggatacttt atccctaaaa tcctgtataa cttc                 44

<210> SEQ ID NO 24
<211> LENGTH: 45
<212> TYPE: DNA
<213> ORGANISM: Artificial Sequence
<220> FEATURE:
<223> OTHER INFORMATION: artificially synthesized primer sequence

<400> SEQUENCE: 24
tccgtagtaa gaaaaactta gggataaagt tcatccaccg atcgg                45

<210> SEQ ID NO 25
<211> LENGTH: 45
<212> TYPE: DNA
<213> ORGANISM: Artificial Sequence
<220> FEATURE:
<223> OTHER INFORMATION: artificially synthesized primer sequence

<400> SEQUENCE: 25
ccgatcggtg gatgaacttt atccctaagt ttttcttact acgga                45

The invention claimed is:

1. A virus vector DNA, wherein a transcription start (S) sequence of at least one gene on the genome of a virus belonging to Paramyxoviridae has been substituted by a different transcription start sequence of another gene of said virus belonging to Paramyxoviridae, so as to modify the expression level of said at least one gene and genes located downstream thereof within a host.

2. The virus vector DNA according to claim 1, wherein said substitution is a substitution of a transcription start sequence of F gene by a transcription start sequence of another gene.

3. The virus vector DNA according to claim 2, wherein said transcription start sequence of another gene is that of a P/M/HN gene type.

4. The virus vector DNA according to claim 1, wherein said substitution is a substitution of transcription start sequences of N gene and/or P gene by a transcription start sequence of another gene.

5. The virus vector DNA according to claim 4, wherein said transcription start sequence of another gene is a transcription start sequence of F gene.

6. A virus vector DNA according to any one of claims 1 or 2–5, wherein said virus vector DNA is defective in F gene and/or HN gene.

7. A virus vector DNA according to any one of claims 1 or 2–5, wherein a foreign gene has been inserted into said virus vector DNA.

8. A virus vector of Paramyxoviridae comprising a transcription product from a virus vector DNA according to any one of claims 1 or 2–5 within virus particles.

9. The vector according to claim 8, wherein said vector is a Sendai virus (SeV) vector.

10. The vector according to claim 8, wherein the proliferation capability in the host is elevated compared to that of the wild type virus.

11. A method for producing a virus vector of Paramyxoviridae, wherein said method comprises the steps of transferring the virus vector DNA according to any one of claims 1 or 2–5 into a host, and expressing viral proteins in said host.

12. The method according to claim 11, wherein said virus of Paramyxoviridae used to produce the vector is Sendai virus.

* * * * *

UNITED STATES PATENT AND TRADEMARK OFFICE
CERTIFICATE OF CORRECTION

PATENT NO. : 7,144,579 B2  
APPLICATION NO. : 09/979908  
DATED : December 5, 2006  
INVENTOR(S) : Nagai et al.

Page 1 of 17

It is certified that error appears in the above-identified patent and that said Letters Patent is hereby corrected as shown below:

Please replace the Sequence Listing in the above-referenced patent, from the beginning of column 29 to the end of column 36, with the Sequence Listing provided below.

SEQUENCE LISTING

```
<110> NAGAI, Yoshiyuki
      KATO, Atsushi
      HASEGAWA, Mamoru
      INOUE, Makoto

<120> PARAMYXOVIRUSES COMPRISING MODIFIED
      TRANSCRIPTION START SEQUENCE

<130> 50026/030001

<140> US 09/979,908
<141> 2001-11-28

<150> PCT/JP00/06051
<151> 2000-09-06

<150> JP 11-252231
<151> 1999-09-06

<160> 54

<170> FastSEQ for Windows Version 4.0
```

Signed and Sealed this

Twenty-seventh Day of April, 2010

David J. Kappos  
*Director of the United States Patent and Trademark Office*

```
<210> 1
<211> 10
<212> DNA
<213> Artificial Sequence

<220>
<223> artificially synthesized oligonucleotide sequence

<400> 1
ctttcaccct                                                                      10

<210> 2
<211> 15
<212> DNA
<213> Artificial Sequence

<220>
<223> artificially synthesized oligonucleotide sequence

<400> 2
tttttcttac tacgg                                                                15

<210> 3
<211> 18
<212> DNA
<213> Artificial Sequence

<220>
<223> artificially synthesized oligonucleotide sequence

<400> 3
gagggcccgc ggccgcga                                                             18

<210> 4
<211> 38
<212> DNA
<213> Artificial Sequence
```

<220>
<223> artificially synthesized primer sequence

<400> 4
gagggcccgc ggccgcgata cgaggcttca aggtactt                    38

<210> 5
<211> 38
<212> DNA
<213> Artificial Sequence

<220>
<223> artificially synthesized primer sequence

<400> 5
tcgcggccgc gggccctctg atcctagatt cctcctac                    38

<210> 6
<211> 48
<212> DNA
<213> Artificial Sequence

<220>
<223> artificially synthesized primer sequence

<400> 6
caaagtatcc accacectga ggagcaggtt ccagaccctt tgctttgc         48

<210> 7
<211> 19
<212> DNA
<213> Artificial Sequence

<220>
<223> artificially synthesized primer sequence

<400> 7
ttaagttggt vagtgactc                                                    19

<210> 8
<211> 64
<212> DNA
<213> Artificial Sequence

<220>
<223> artificially synthesized primer sequence

<400> 8
ttgcggccgc gtaagaaaaa cttagggtga aagttcactt cacgatggaa gacggcaaaa    60
acat                                                                   64

<210> 9
<211> 64
<212> DNA
<213> Artificial Sequence

<220>
<223> artificially synthesized primer sequence

<400> 9
ttgcggccgc gtaagaaaaa cttagggtca aagttcactt cacgatggaa gacggcaaaa    60
acat                                                                   64

<210> 10
<211> 64
<212> DNA
<213> Artificial Sequence

<220>
<223> artificially synthesized primer sequence

```
<400> 10
ttgcggccgc gtaagaaaaa cttagggata aagttcactt cacgatggaa gacggcaaaa    60
acat                                                                 64

<210> 11
<211> 64
<212> DNA
<213> Artificial Sequence

<220>
<223> artificially synthesized primer sequence

<400> 11
ttgcggccgc gtaagaaaaa cttagggtga atgttcactt cacgatggaa gacggcaaaa    60
acat                                                                 64

<210> 12
<211> 31
<212> DNA
<213> Artificial Sequence

<220>
<223> artificially synthesized primer sequence

<400> 12
tcgcggccgc tattacaatt tggactttcc g                                   31

<210> 13
<211> 21
<212> DNA
<213> Artificial Sequence

<220>
<223> artificially synthesized primer sequence

<400> 13
cttagggtga aagtcccttg t                                              21
```

<210> 14
<211> 21
<212> DNA
<213> Artificial Sequence

<220>
<223> artificially synthesized primer sequence

<400> 14
acaagggact tcaccctaa g                    21

<210> 15
<211> 21
<212> DNA
<213> Artificial Sequence

<220>
<223> artificially synthesized primer sequence

<400> 15
tacccatagg tgtggccaaa t                    21

<210> 16
<211> 21
<212> DNA
<213> Artificial Sequence

<220>
<223> artificially synthesized primer sequence

<400> 16
taatacgact cactataggg c                    21

<210> 17
<211> 20
<212> DNA
<213> Artificial Sequence

<220>
<223> artificially synthesized primer sequence

<400> 17
ttttctcact tgggttaatc                                           20

<210> 18
<211> 20
<212> DNA
<213> Artificial Sequence

<220>
<223> artificially synthesized primer sequence

<400> 18
gcactcacaa gggactttca                                           20

<210> 19
<211> 20
<212> DNA
<213> Artificial Sequence

<220>
<223> artificially synthesized primer sequence

<400> 19
gcactcacaa gggactttat                                           20

<210> 20
<211> 34
<212> DNA
<213> Artificial Sequence

<220>
<223> artificially synthesized primer sequence

<400> 20
tcgacaccag gtatttaaat taattaatcg cgag                       34

<210> 21
<211> 34
<212> DNA
<213> Artificial Sequence

<220>
<223> artificially synthesized primer sequence

<400> 21
ctagctcgcg attaattaat ttaaatacct ggtg                       34

<210> 22
<211> 44
<212> DNA
<213> Artificial Sequence

<220>
<223> artificially synthesized primer sequence

<400> 22
gaagttatac aggattttag ggataaagta tccaccctga ggag            44

<210> 23
<211> 44
<212> DNA
<213> Artificial Sequence

<220>
<223> artificially synthesized primer sequence

<400> 23
ctcctcaggg tggatacttt atccctaaaa tcctgtataa cttc            44

<210> 24

<211> 45
<212> DNA
<213> Artificial Sequence

<220>
<223> artificially synthesized primer sequence

<400> 24
tccgtagtaa gaaaaactta gggataaagt tcatccaccg atcgg          45

<210> 25
<211> 45
<212> DNA
<213> Artificial Sequence

<220>
<223> artificially synthesized primer sequence

<400> 25
ccgatcggtg gatgaacttt atccctaagt ttttcttact acgga          45

<210> 26
<211> 10
<212> RNA
<213> Sendai virus

<400> 26
uuuuuucuua          10

<210> 27
<211> 10
<212> RNA
<213> Sendai virus

<400> 27
cwuuvwcccu          10

```
<210> 28
<211> 10
<212> RNA
<213> Sendai virus

<400> 28
cuuucacccu                                                              10

<210> 29
<211> 10
<212> RNA
<213> Sendai virus

<400> 29
cuuugacccu                                                              10

<210> 30
<211> 10
<212> RNA
<213> Sendai virus

<400> 30
cuuuaucccu                                                              10

<210> 31
<211> 10
<212> RNA
<213> Sendai virus

<400> 31
cauucacccu                                                              10

<210> 32
<211> 9
<212> DNA
<213> Artificial Sequence
```

<220>
<223> a DNA encoding a part of Sendai virus genome

<400> 32
taagaaaaa            9

<210> 33
<211> 10
<212> DNA
<213> Artificial Sequence

<220>
<223> a DNA encoding a part of Sendai virus genome

<400> 33
agggtgaaag           10

<210> 34
<211> 10
<212> DNA
<213> Artificial Sequence

<220>
<223> a DNA encoding a part of Sendai virus genome

<400> 34
agggtcaaag           10

<210> 35
<211> 10
<212> DNA
<213> Artificial Sequence

<220>
<223> a DNA encoding a part of Sendai virus genome

```
<400> 35
agggataaag                                                      10

<210> 36
<211> 10
<212> DNA
<213> Artificial Sequence

<220>
<223> a DNA encoding a part of Sendai virus genome

<400> 36
agggtgaatg                                                      10

<210> 37
<211> 54
<212> DNA
<213> Artificial Sequence

<220>
<223> a DNA encoding a part of Sendai virus genome

<400> 37
accaaacagg agaaaaacat gtatgggata tgtaatgaag ttatacagga tttt      54

<210> 38
<211> 14
<212> DNA
<213> Artificial Sequence

<220>
<223> a DNA encoding a part of Sendai virus genome

<400> 38
agggtcaaag tatc                                                 14
```

<210> 39
<211> 15
<212> DNA
<213> Artificial Sequence

<220>
<223> a DNA encoding a part of Sendai virus genome

<400> 39
tagtaagaaa aactt                                                        15

<210> 40
<211> 14
<212> DNA
<213> Artificial Sequence

<220>
<223> a DNA encoding a part of Sendai virus genome

<400> 40
agggtgaaag ttca                                                         14

<210> 41
<211> 15
<212> DNA
<213> Artificial Sequence

<220>
<223> a DNA encoding a part of Sendai virus genome

<400> 41
gattaagaaa aactt                                                        15

<210> 42
<211> 14
<212> DNA
<213> Artificial Sequence

<220>
<223> a DNA encoding a part of Sendai virus genome

<400> 42
agggtgaaag aaat                                              14

<210> 43
<211> 15
<212> DNA
<213> Artificial Sequence

<220>
<223> a DNA encoding a part of Sendai virus genome

<400> 43
aaataagaaa aactt                                             15

<210> 44
<211> 14
<212> DNA
<213> Artificial Sequence

<220>
<223> a DNA encoding a part of Sendai virus genome

<400> 44
agggataaag tccc                                              14

<210> 45
<211> 15
<212> DNA
<213> Artificial Sequence

<220>
<223> a DNA encoding a part of Sendai virus genome

<400> 45

```
taataagaaa aactt                                          15

<210> 46
<211> 14
<212> DNA
<213> Artificial Sequence

<220>
<223> a DNA encoding a part of Sendai virus genome

<400> 46
agggtgaaag tgag                                           14

<210> 47
<211> 15
<212> DNA
<213> Artificial Sequence

<220>
<223> a DNA encoding a part of Sendai virus genome

<400> 47
tattaagaaa aaccc                                          15

<210> 48
<211> 14
<212> DNA
<213> Artificial Sequence

<220>
<223> a DNA encoding a part of Sendai virus genome

<400> 48
agggtgaatg ggaa                                           14

<210> 49
<211> 15
```

<212> DNA
<213> Artificial Sequence

<220>
<223> a DNA encoding a part of Sendai virus genome

<400> 49
tagtaagaaa aactt                                                          15

<210> 50
<211> 54
<212> DNA
<213> Artificial Sequence

<220>
<223> a DNA encoding a part of Sendai virus genome

<400> 50
acaagaagac aagaaaattt aaaaggatac atatctctta aactcttgtc tggt              54

<210> 51
<211> 10
<212> DNA
<213> Artificial Sequence

<220>
<223> Artificially synthesized sequence

<400> 51
ctttatccct                                                                10

<210> 52
<211> 10
<212> DNA
<213> Artificial Sequence

<220>
<223> Artificially synthesized sequence

<400> 52
ctttcaccct					10

<210> 53
<211> 34
<212> DNA
<213> Artificial Sequence

<220>
<223> Artificially synthesized sequence

<400> 53
tcgacaccag gtatttaaat taattaatcg cgag					34

<210> 54
<211> 34
<212> DNA
<213> Artificial Sequence

<220>
<223> Artificially synthesized sequence

<400> 54
ctagctcgcg attaattaat ttaaatacct ggtg					34